United States Patent
Nguyen et al.

(10) Patent No.: US 9,482,944 B2
(45) Date of Patent: Nov. 1, 2016

(54) COPOLYMERS, POLYMERIC PARTICLES COMPRISING SAID COPOLYMERS AND COPOLYMERIC BINDERS FOR RADIATION-SENSITIVE COATING COMPOSITIONS FOR NEGATIVE-WORKING RADIATION-SENSITIVE LITHOGRAPHIC PRINTING PLATES

(75) Inventors: My T. Nguyen, Kirkland (CA); Marc-Andre Locas, Pierrefonds (CA)

(73) Assignee: MYLAN GROUP, Travinh, Travinh Province (VN)

(*) Notice: Subject to any disclaimer, the term of this patent is extended or adjusted under 35 U.S.C. 154(b) by 0 days.

(21) Appl. No.: 13/391,363

(22) PCT Filed: Sep. 14, 2010

(86) PCT No.: PCT/CA2010/001400
§ 371 (c)(1),
(2), (4) Date: Feb. 20, 2012

(87) PCT Pub. No.: WO2010/148520
PCT Pub. Date: Dec. 29, 2010

(65) Prior Publication Data
US 2012/0190810 A1     Jul. 26, 2012

Related U.S. Application Data

(60) Provisional application No. 61/242,421, filed on Sep. 15, 2009.

(51) Int. Cl.
*C08F 220/50* (2006.01)
*G03F 7/029* (2006.01)
(Continued)

(52) U.S. Cl.
CPC ............ *G03F 7/029* (2013.01); *B41C 1/1008* (2013.01); *C07C 233/18* (2013.01);
(Continued)

(58) Field of Classification Search
CPC .. C08F 222/42; C08F 222/50; C08F 220/42; C08F 220/50; C08F 220/70; C08F 220/60
USPC ........................................ 526/297, 298, 299
See application file for complete search history.

(56) References Cited

U.S. PATENT DOCUMENTS 2,839,511 A *   6/1958   Harris et al. ............... 526/298
3,933,715 A     1/1976   Botsch et al.
(Continued)

FOREIGN PATENT DOCUMENTS

CN     101479663 A     6/2009
EP     0083971 A2     7/1983
(Continued)

OTHER PUBLICATIONS

Urankar, Edward et al. "Photogenerated Base in Polymer Curring and Imaging:Cross-linking of Base SEnsitive Polymer Containing Enolizable Pendant Groups" 1997, Chem. Mater., 9, 2861-2868.*
(Continued)

*Primary Examiner* — Ling Choi
*Assistant Examiner* — David L Miller
(74) *Attorney, Agent, or Firm* — Lathrop & Gage LLP; Brian C. Trinque

(57) ABSTRACT

There is provided a copolymer and polymeric particle comprising the copolymer, a method of producing a polymeric particle, a copolymeric binder, a method of producing a copolymeric binder, a near infrared radiation-sensitive coating composition, a negative working lithographic offset printing plate, a method of producing a negative working lithographic offset printing plate and methods of imaging the plate and printing with the imaged plate.

12 Claims, 3 Drawing Sheets

(51) Int. Cl.

| | |
|---|---|
| *C08F 220/70* | (2006.01) |
| *C08F 220/60* | (2006.01) |
| *B41C 1/10* | (2006.01) |
| *C07C 233/18* | (2006.01) |
| *C07C 255/19* | (2006.01) |
| *C07C 255/33* | (2006.01) |
| *C07C 271/16* | (2006.01) |
| *C07C 271/28* | (2006.01) |
| *C07C 275/10* | (2006.01) |
| *C07D 207/40* | (2006.01) |
| *C07D 295/215* | (2006.01) |
| *C07F 9/09* | (2006.01) |
| *C08F 220/42* | (2006.01) |
| *G03F 7/027* | (2006.01) |
| *G03F 7/033* | (2006.01) |
| *C08F 212/08* | (2006.01) |
| *C08F 220/06* | (2006.01) |
| *C08F 230/02* | (2006.01) |

(52) U.S. Cl.
CPC .......... *C07C 255/19* (2013.01); *C07C 255/33* (2013.01); *C07C 271/16* (2013.01); *C07C 271/28* (2013.01); *C07C 275/10* (2013.01); *C07D 207/40* (2013.01); *C07D 295/215* (2013.01); *C07F 9/091* (2013.01); *C08F 220/42* (2013.01); *C08F 220/50* (2013.01); *C08F 220/60* (2013.01); *C08F 220/70* (2013.01); *G03F 7/027* (2013.01); *G03F 7/033* (2013.01); *B41C 2210/04* (2013.01); *B41C 2210/08* (2013.01); *B41C 2210/22* (2013.01); *B41C 2210/24* (2013.01); *C08F 212/08* (2013.01); *C08F 220/06* (2013.01); *C08F 230/02* (2013.01)

(56) References Cited

U.S. PATENT DOCUMENTS

| | | | |
|---|---|---|---|
| 4,297,431 A | 10/1981 | Sullivan | |
| 4,345,017 A | 8/1982 | Cournoyer et al. | |
| 5,397,690 A | 3/1995 | Fabricius et al. | |
| 5,569,573 A | 10/1996 | Takahashi et al. | |
| 5,807,932 A | 9/1998 | Pfaendner et al. | |
| 5,955,539 A * | 9/1999 | Nishikawa | 525/63 |
| 6,107,488 A | 8/2000 | Bouchet et al. | |
| 6,124,425 A | 9/2000 | Nguyen | |
| 6,132,929 A | 10/2000 | Nakamura et al. | |
| 6,177,182 B1 | 1/2001 | Nguyen | |
| 6,261,740 B1 | 7/2001 | Nguyen et al. | |
| 6,326,122 B1 | 12/2001 | Nagasaka et al. | |
| 6,355,396 B1 | 3/2002 | Nakamura | |
| 6,410,203 B1 | 6/2002 | Nakamura | |
| 6,582,882 B2 | 6/2003 | Pappas et al. | |
| 6,805,052 B2 | 10/2004 | Aert et al. | |
| 6,846,614 B2 | 1/2005 | Timpe et al. | |
| 6,884,568 B2 | 4/2005 | Timpe et al. | |
| 6,899,994 B2 | 5/2005 | Huang et al. | |
| 6,960,422 B2 | 11/2005 | Goto | |
| 6,969,575 B2 | 11/2005 | Inno | |
| 6,983,694 B2 | 1/2006 | Vermeersch et al. | |
| 7,001,704 B2 | 2/2006 | Oshima et al. | |
| 7,060,415 B2 | 6/2006 | Kitson et al. | |
| 7,060,416 B2 | 6/2006 | Ray et al. | |
| 7,258,961 B2 | 8/2007 | Oda et al. | |
| 7,261,998 B2 | 8/2007 | Hayashi et al. | |
| 7,371,504 B2 | 5/2008 | Nakamura | |
| 7,473,515 B2 | 1/2009 | Nguyen et al. | |
| 8,084,564 B2 | 12/2011 | Kano et al. | |

| | | | |
|---|---|---|---|
| 2002/0160299 A1 | 10/2002 | Asawa et al. | |
| 2005/0123853 A1 | 6/2005 | Munnelly et al. | |
| 2007/0134590 A1 | 6/2007 | Fukuhara et al. | |
| 2007/0269739 A1 | 11/2007 | Nguyen et al. | |
| 2008/0139737 A1 | 6/2008 | Alderfer et al. | |
| 2008/0171286 A1 | 7/2008 | Nguyen et al. | |
| 2009/0035694 A1 | 2/2009 | Nguyen et al. | |
| 2009/0111051 A1 | 4/2009 | Tao et al. | |
| 2009/0186299 A1 | 7/2009 | Tao et al. | |
| 2010/0021844 A1 * | 1/2010 | Yu et al. | 430/273.1 |
| 2012/0190810 A1 | 7/2012 | Nguyen et al. | |

FOREIGN PATENT DOCUMENTS

| | | | |
|---|---|---|---|
| EP | 0550998 A1 | 12/1992 | |
| EP | 1 136 886 A1 | 9/2001 | |
| EP | 0 770 495 B1 | 6/2002 | |
| EP | 1429184 A1 | 6/2004 | |
| EP | 1437232 B1 | 1/2007 | |
| GB | 780284 | 7/1957 | |
| JP | 62063595 | 3/1987 | |
| JP | H10287823 A | 10/1998 | |
| JP | 11119427 A * | 4/1999 | |
| JP | 2008/083159 A | 4/2008 | |
| JP | 2008/299350 A | 12/2008 | |
| JP | 2009046624 A | 3/2009 | |
| JP | 2009191107 A * | 8/2009 | |
| JP | 2010/002762 A | 1/2010 | |
| KR | 10-2009-0073079 A | 7/2009 | |
| WO | 2006007270 A1 | 1/2006 | |
| WO | 2008048749 A2 | 4/2008 | |
| WO | WO2011050442 A1 | 5/2011 | |
| WO | WO2011050442 A2 | 5/2011 | |

OTHER PUBLICATIONS

Urankar, et al.; Photogenerated Base in Polymer Curing and Imaging: Cross-Linking of Base-Sensitive Polymers Containing Enolizable Pendant Groups; Cehm. Mater.; 1997; 9: 2861-2868.

Reghunadhan, et al.; Advances in Polymer Science; 2001; ISBN 3-540-41435-5; Springer-Verlag Berlin heidelberg New York; Library of Congress Catalog Card No. 61642; (2001); p. 64 (3 pages).

Chiang, et al.; Copolymerization of N-(4-Carboxyphenyl)-maleimide with Acrylonitrile and the Properties of its Membrane; J. Polymer Research; (2000) vol. 7, No. 4; pp. 251-255.

Zhang, et al.; The Electropolymerization of Poly(styrene-co-4-carbosyphenyl maleimide) Coatings onto Steel; J. Applied Polymer Sci.; (1996); vol. 62; pp. 1303-1312.

Mitsuishi, et al.; Mechanical Properties of Polypropylene Filled with Calcium Carbonate; Polymer Engineering and Science; (1985); vol. 25; No. 17; pp. 1069-1073.

CAS No. 6976-93-8, American Chemical Society, 2012, 3 pages.
CAS No. 923-26-2, American Chemical Society, 2012, 3 pages.
CAS No. 868-77-9, American Chemical Society, 2012, 6 pages.
Sun, et al.; Durable and Refreshable Polymeric N-Halamine Biocides Containing 3-(4'-vinylbenzyl)-5,5-dimethylhydantoin; J. Polymer Sci; (2001); vol. 30, pp. 3348-3355.
CAS No. 100-42-5, American Chemical Society, 2012, 10 pages.
CAS No. 1484-13.5, American Chemical Society, 2012, 4 pages.
International Search Report and Written Opinion, PCT/CA2010/001400, Dec. 15, 2010, 12 pages.
International Search Report and Written Opinion, PCT/CA2010/001401, Jun. 2, 2011, 12 pages.
CAS Registry No. 346587-51-7, American Chemical Company, 2014, 1 page.
U.S. Appl. No. 13/822,976, filed Mar. 13, 2013, My T. Nguyen.
European Supplementary Search Report as it relates to PCT/CA2010001400, dated Mar. 18, 2015.

* cited by examiner

COPOLYMERS, POLYMERIC PARTICLES COMPRISING SAID COPOLYMERS AND COPOLYMERIC BINDERS FOR RADIATION-SENSITIVE COATING COMPOSITIONS FOR NEGATIVE-WORKING RADIATION-SENSITIVE LITHOGRAPHIC PRINTING PLATES

CROSS-REFERENCE TO RELATED APPLICATIONS

This application is a National Entry Application of PCT application no PCT/CA2010/001400 filed on Sep. 14, 2010 and published in English under PCT Article 21(2), which itself claims benefit of U.S. provisional application Ser. No. 61/242,421, filed on Sep. 15, 2009. All documents above are incorporated herein in their entirety by reference.

FIELD OF THE INVENTION

The present invention relates to radiation-sensitive lithographic printing plates and their coatings. More specifically, the invention relates to copolymers, polymeric particles comprising these copolymers and copolymeric binders for use in radiation-sensitive coating compositions for negative-working radiation-sensitive lithographic printing plates.

BACKGROUND OF THE INVENTION

In lithographic printing, a printing plate is mounted on the cylinder of a printing press. The printing plate carries a lithographic image on its surface and a printed copy is obtained by applying ink to the image and then transferring the ink from the printing plate onto a receiver material, which typically is a sheet of paper. Generally, the ink is first transferred to an intermediate blanket, which in turn transfers the ink to the surface of the receiver material (offset printing).

In conventional, so-called "wet" lithographic printing, ink as well as an aqueous fountain solution (also called dampening liquid) are supplied to the lithographic image which consists of oleophilic (or hydrophobic, i.e. ink-accepting, water-repelling) areas as well as hydrophilic (or oleophobic, i.e. water-accepting, ink-repelling) areas. When the surface of the printing plate is moistened with water and ink is applied, the hydrophilic regions retain water and repel ink, and the ink-receptive regions accept ink and repel water. During printing, the ink is transferred to the surface of the receiver material upon which the image is to be reproduced.

Lithographic printing plates typically comprise an imageable layer (also called imaging layer or coating) applied over the hydrophilic surface of a substrate, typically aluminium. The imageable layer includes one or more radiation-sensitive components, often dispersed in a suitable binder.

To produce the lithographic image on the printing plate, the printing plate is imaged by targeted radiation. This can be carried out in different ways. In direct digital imaging (computer-to-plate), printing plates can be imaged with infrared or UV lasers or light sources. Such a laser beam can be digitally controlled via a computer; i.e. the laser can be turned on or off so that imagewise exposure of the precursor can be affected via stored digitized information in the computer. Therefore, the imageable layers of printing plates, which are to be imagewise exposed by means of such image-setters, need to be sensitive to radiation in the near-infrared (NIR) or ultraviolet (UV) regions of the spectrum.

The imaging device will etch the image on the printing plate by eliciting a localized transformation of the imageable layer. Indeed, in such imaged systems, the imageable layer typically contains a dye or pigment that absorbs the incident radiation and the absorbed energy initiates the reaction producing the image. Exposure to radiation triggers a physical or chemical process in the imageable layer so that the imaged areas become different from the non-imaged areas and development will produce an image on the printing plate. The change in the imageable layer can be a change of hydrophilicity/oleophilicity, solubility, hardness, etc.

Following exposure, either the exposed regions or the unexposed regions of the imageable layer are removed by a suitable developer, revealing the underlying hydrophilic surface of the substrate. Developers are typically aqueous alkaline solutions, which may also contain organic solvents.

Alternatively, "on-press developable" lithographic printing plate can be directly mounted on a press after imaging, and are developed through contact with ink and/or fountain solution during initial press operation. In other words, either the exposed regions or the unexposed regions of the imageable layer are removed by the ink and/or fountain solution, not by a developer. More specifically, a so-called on-press development system is one in which an exposed printing plate is fixed on the plate cylinder of a printing press, and a fountain solution and ink are fed thereto while revolving the cylinder to remove non-image areas. This technique allows an imaged, but un-developed printing plate (also called a printing plate precursor) to be mounted as is on a press and be made into a printing plate on an ordinary printing line.

If the exposed regions are removed, the precursor is positive working. Conversely, if the unexposed regions are removed, the precursor is negative working. In each instance, the regions of the imageable layer (i.e., the image areas) that remain are ink-receptive, and the regions of the hydrophilic surface revealed by the developing process accept water and aqueous solutions, typically a fountain solution, and do not accept ink.

Negative-working lithographic printing plates using a variety of polymers, copolymers, polymeric particles and binders have already been developed. However, there remains a need for new materials and new coatings for such plates.

SUMMARY OF THE INVENTION

In accordance with the present invention, there is provided:
1. A copolymer comprising:
   monomer units A comprising a cyano-containing pendant group in which the cyano is not directly attached to the backbone of the copolymer;
   monomer units B comprising a film-forming pendant group;
   monomer units C comprising a poly(ethylene glycol), poly(propylene glycol) and/or poly(ethylene glycol ran propylene glycol) containing side chain, said side chain being attached to the backbone of the copolymer via an amide, a carbamate, an ester or an urea linker; and
   optionally, monomer units D comprising at least one functional group capable of undergoing a crosslinking reaction via cationic polymerization.
2. The copolymer of item 1 being of formula:

Formula 1

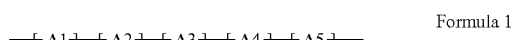

wherein:
   a, c, and d are molar ratios varying between about 0.01 and about 0.90;
   b and e are molar ratios varying between about 0 and about 0.90;
   A1 represents monomer units A;

A2 represents monomer units A or monomer units B;
A3 represents monomer units C;
A4 represents monomer units B; and
A5 represents monomer units B or monomer units D,
wherein monomer units A in A1 and A2 are different from each other and wherein monomer units B in A2, A4 and A5 are different from each other.

3. The copolymer of item 1 or 2, wherein monomer units A are of formula:

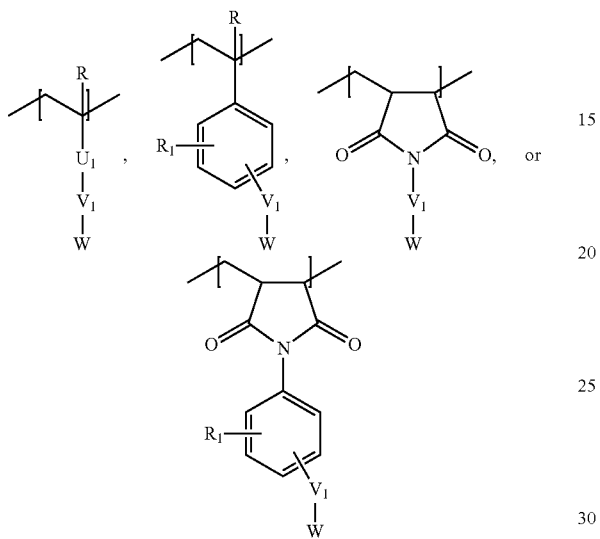

wherein:
R is hydrogen, methyl or ethyl;
$R_1$ is absent or represents one to four alkyl or alkyloxy substituents, the alkyl and alkyloxy substituents optionally comprising one or more ether, ester, amine, amide, urea, piperazinyl, sulfonamide, or carbamate functional groups, the alkyl and alkyloxy substituents optionally being substituted with one or more cyano;
$U_1$ is an amide or ester linker;
$V_1$ is absent or represents alkyl optionally comprising one or more ether, ester, amine, amide, urea, piperazinyl, or carbamate functional group, the alkyl optionally being substituted with one or more cyano; and
W is —CN or

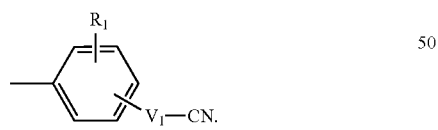

4. The copolymer of item 3, wherein monomer units A are of formula:

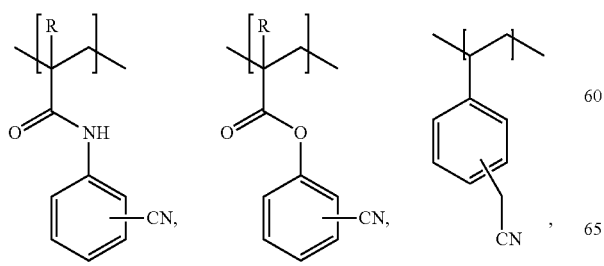

-continued

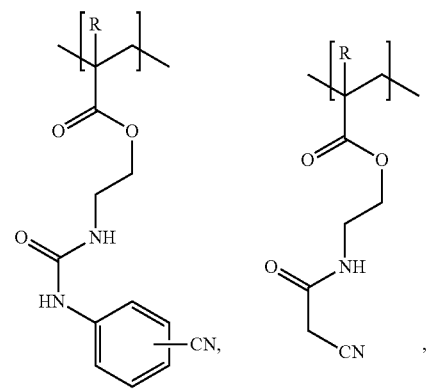

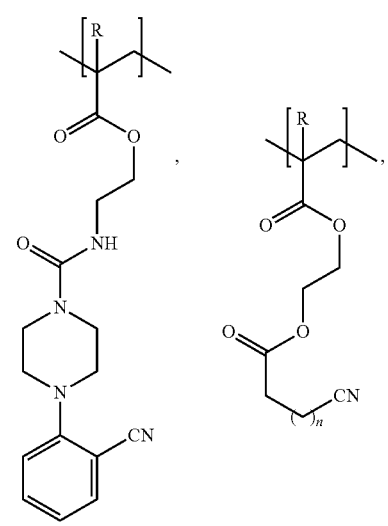

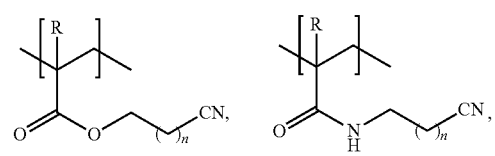

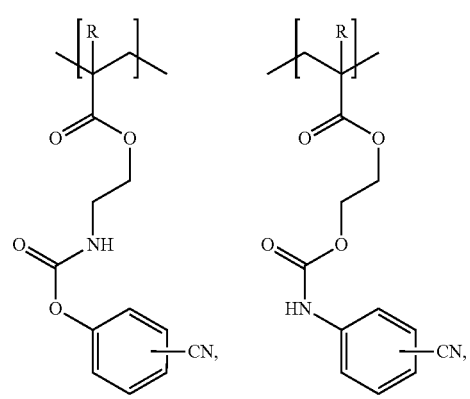

-continued

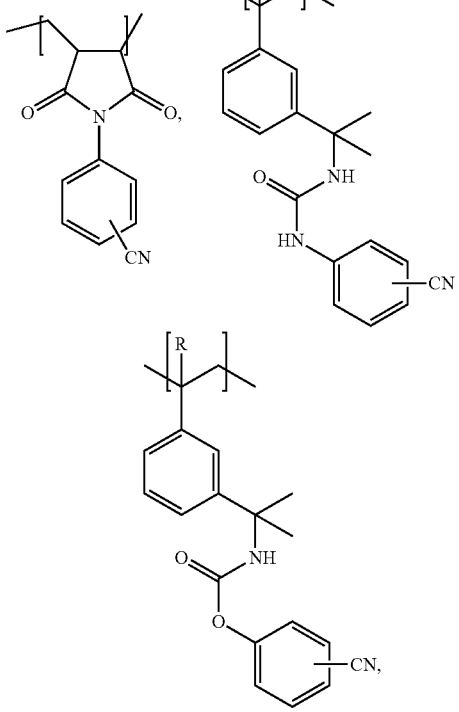

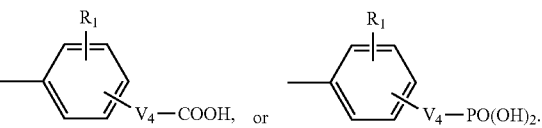, or wherein R is hydrogen, methyl or ethyl and n varies between 1 and 10.

5. The copolymer of any one of items 1 to 4, wherein the copolymer comprises monomer units B of formula:

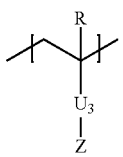

wherein
R is hydrogen, methyl or ethyl;
$U_3$ is absent or represents an amide or ester linker; and
Z is alkyl or aryl,
the alkyl being optionally substituted with one or more hydroxyl, alkyloxy or halide, and
the aryl being optionally substituted with one or more alkyls that are optionally substituted with one or more hydroxyl, alkyloxy or halide.

6. The copolymer or any one of items 1 to 5, wherein the copolymer comprises monomer units B of formula:

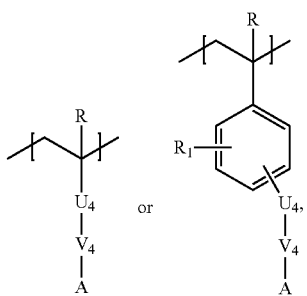

wherein R is hydrogen, methyl or ethyl,
$R_1$ is absent or represents one to four alkyl substituents;
the alkyl substituents optionally comprising one or more ether, ester, amine, amide, urea, piperazinyl, sulfonamide, or carbamate functional groups;
$U_4$ is absent or represents an amide or ester linker;
$V_4$ is absent or represents alkyl optionally comprising one or more ether, ester, amine, amide, urea, piperazinyl, sulfonamide or carbamate functional group; and
A is —COOH, —PO(OH)$_2$,

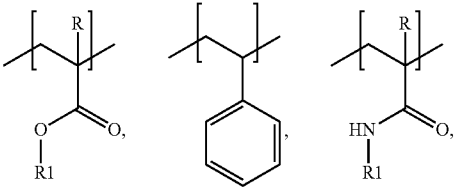

7. The copolymer of any one of item 1 to 6, wherein monomer units B are of formula:

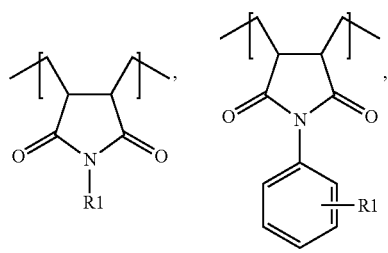

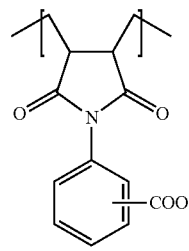

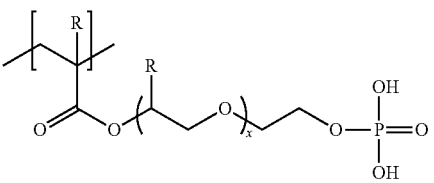

wherein
R is hydrogen or methyl;
R1 is hydrogen or alkyl; and
x is a number of repeating units between 1 and 10.

8. The copolymer of any one of items 1 to 7, wherein monomer units C are terminated by a hydroxyl group, a methoxy group or a substituent comprising a cyano group.

9. The copolymer of item 8, wherein monomer units C are of formula:

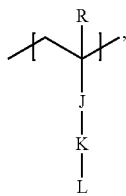

wherein:
R is hydrogen, methyl or ethyl;
J is absent or represents an amide, ester, carbamate or urea linker; and
K and L together form said side chain, K comprising a poly(ethylene glycol), poly(propylene glycol) and/or poly(ethylene glycol ran propylene glycol) chain, and L being —OH, —OCH₃, —CN or

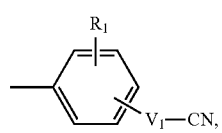

wherein $R_1$ is absent or represents one to four alkyl or alkyloxy substituents, the alkyl and alkyloxy substituents optionally comprising one or more ether, ester, amine, amide, urea, piperazinyl, sulfonamide, or carbamate functional groups, the alkyl and alkyloxy substituents optionally being substituted with one or more cyano; and $V_1$ is absent or represents alkyl optionally comprising one or more ether, ester, amine, amide, urea, piperazinyl, or carbamate functional group, the alkyl optionally being substituted with one or more cyano.

10. The copolymer of item 9, wherein one or more ether, ester, amine, amide, urea, piperazinyl, or carbamate linker is attached at either or both ends of the poly(ethylene glycol), poly(propylene glycol) and/or poly(ethylene glycol ran propylene glycol) chain.

11. The copolymer of item 9 or 10, wherein an alkyl is attached at either or both ends of the poly(ethylene glycol), poly(propylene glycol) and/or poly(ethylene glycol ran propylene glycol) chain, said alkyl optionally comprising one or more ether, ester, amine, amide, urea, piperazinyl, or carbamate functional group.

12. The copolymer of any one of items 1 to 11, wherein monomer units C are of formula:

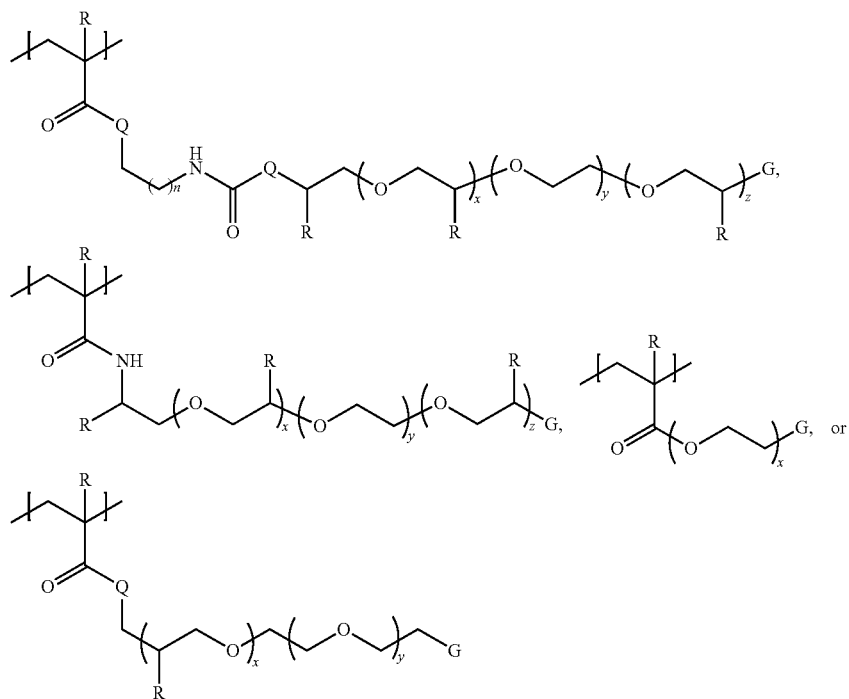

wherein:
R is independently hydrogen, methyl or ethyl;
x, y, and n vary from 1 to 20;
z varies from 0 to 20;
Q is independently —O—,

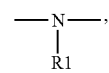

or —O—CH₂CH₂—NH—C(=O)—NH—CH₂—;
and
G is:
hydroxyl,
methoxy,

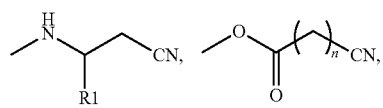

-continued

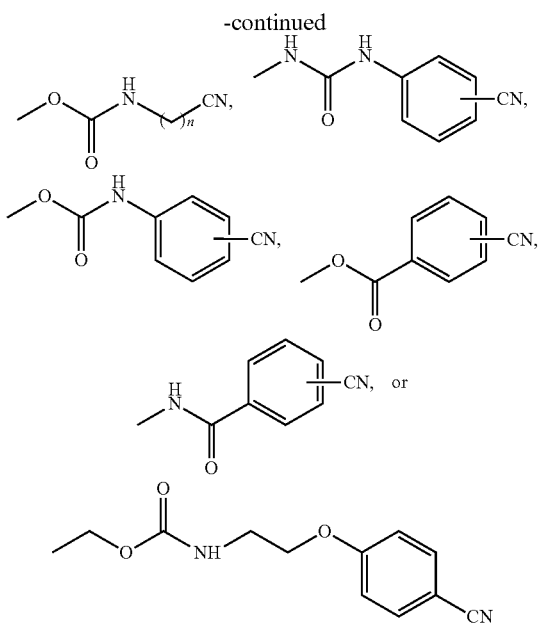

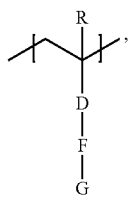

wherein n is as defined above, and
wherein R1 in Q and G is hydrogen or alkyl.

13. The copolymer of any one of items 1 to 12, wherein the at least one functional group capable of undergoing a crosslinking reaction via cationic polymerization is N-alkoxymethylamido (such as N-methoxymethylamido), N-hydroxymethylamido, N-alkoxymethylacrylamide (such as N-methoxymethylacrylamide), N-alkoxymethylmethacrylamide (such as N-methoxymethylmethacrylamide), hydroxyl, alkoxy, hydroxyalkyl, epoxy, or oxetane.

14. The copolymer of item 12, wherein monomer units D are of formula:

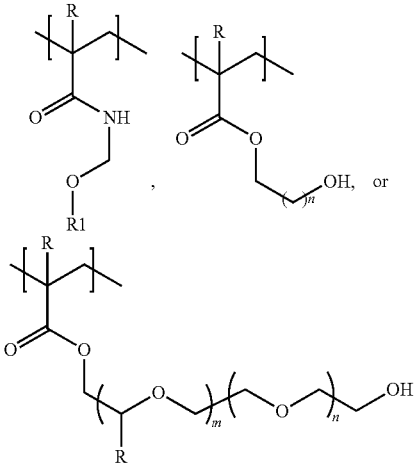

wherein:
R is hydrogen, methyl or ethyl,
E is absent or represents an amide or ester linker;
F is alkyl optionally comprising one or more ether, ester, amine, amide, urea, piperazinyl, or carbamate functional group;
or a poly(ethylene glycol), poly(propylene glycol) and/or poly(ethylene glycol ran propylene glycol) chain, the chain optionally having attached at either or both ends an alkyl optionally comprising one or more ether, ester, amine, amide, urea, piperazinyl, or carbamate functional group; and
G is the functional group capable of undergoing a crosslinking reaction via cationic polymerization.

15. The copolymer of any one of items 1 to 14, wherein monomer units D are of formula:

wherein:
R is hydrogen, methyl or ethyl;
R1 is hydrogen or alkyl; and
m and n vary from 1 to 50.

16. The copolymer of any one of items 1 to 15, wherein A5 represents monomer units D.

17. The copolymer of any one of items 1 to 16, wherein the copolymer is in the form of polymeric particles.

18. The copolymer of item 17, wherein the polymeric particles have a particle size between about 80 and about 1000 nm 19. The copolymer of item 18, wherein the polymeric particles have a particle size between about 150 and about 300 nm.

20. A copolymeric binder comprising:
monomer units A comprising a cyano-containing pendant group in which the cyano is not directly attached to the backbone of the copolymeric binder;
monomer units B comprising a film-forming pendant group; and
optionally, monomer units D comprising at least one functional group capable of undergoing a crosslinking reaction via cationic polymerization.

21. The copolymeric binder of item 20 being of formula:

Formula 2

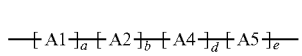

wherein:
a and d are molar ratios varying between about 0.01 and about 0.90;
b and e are molar ratios varying between about 0 and about 0.90;
A1 represents monomer units A;
A2 represents monomer units A or monomer units B;
A4 represents monomer units B; and
A5 represents monomer units B or monomer units D,
wherein monomer units A in A1 and A2 are independent from each other and wherein monomer units B in A2, A4 and A5 are independent from each other.

22. The copolymeric binder of item 20 or 21, wherein monomer units A are of formula:

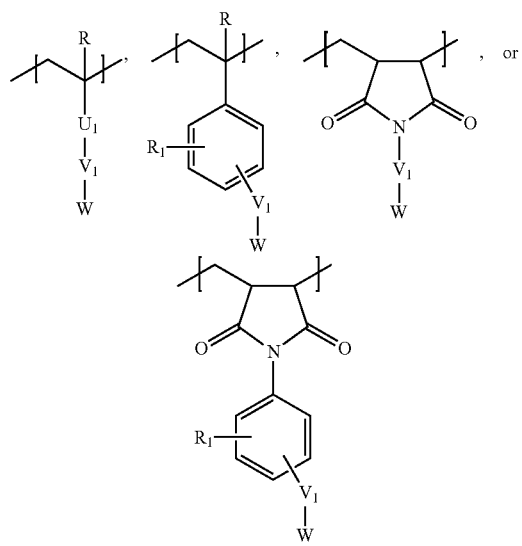

wherein:
R is hydrogen, methyl or ethyl;
$R_1$ is absent or represents one to four alkyl or alkyloxy substituents, the alkyl and alkyloxy substituents optionally comprising one or more ether, ester, amine, amide, urea, piperazinyl, sulfonamide, or carbamate functional groups, the alkyl and alkyloxy substituents optionally being substituted with one or more cyano;
$U_1$ is an amide or ester linker;
$V_1$ is absent or represents alkyl optionally comprising one or more ether, ester, amine, amide, urea, piperazinyl, or carbamate functional group, the alkyl optionally being substituted with one or more cyano; and
W is —CN or

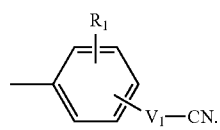

23. The copolymeric binder of any one of items 20 to 22, wherein monomer units A are of formula:

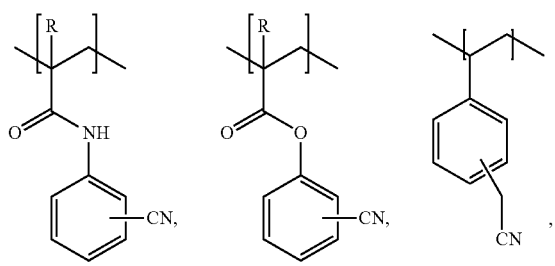

-continued

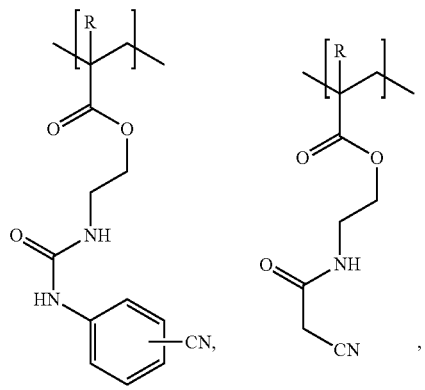

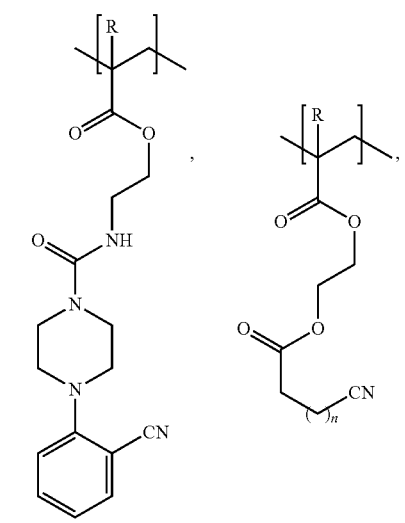

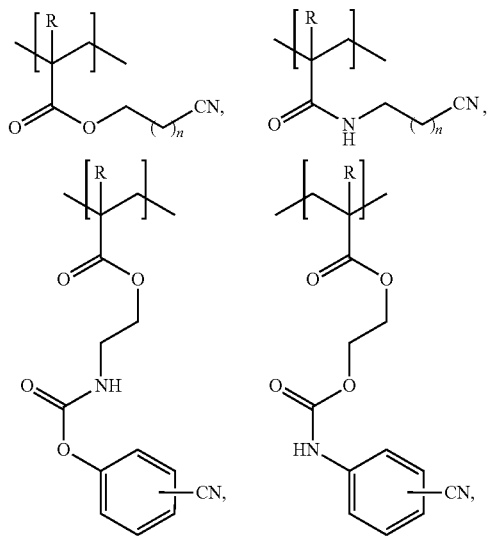

-continued

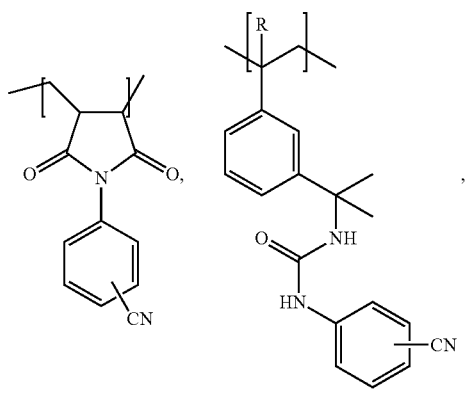

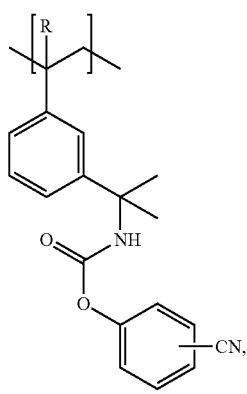

wherein R is hydrogen, methyl or ethyl and n varies between 1 and 10.

24. The copolymeric binder of any one of items 20 to 23, wherein the copolymeric binder comprises monomer unit B of formula:

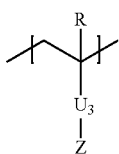

wherein

R is hydrogen, methyl or ethyl;

$U_3$ is absent or represents an amide or ester linker; and

Z is alkyl or aryl, the alkyl being optionally substituted with one or more hydroxyl, alkyloxy or halide, and the aryl being optionally substituted with one or more alkyls that are optionally substituted with one or more hydroxyl, alkyloxy or halide.

25. The copolymeric binder of any one of items 20 to 24, wherein the copolymeric binder monomer units B of formula:

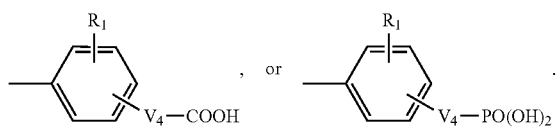

wherein

R is hydrogen, methyl or ethyl;

$R_1$ is absent or represents one to four alkyl substituents; the alkyl substituents optionally comprising one or more ether, ester, amine, amide, urea, piperazinyl, sulfonamide, or carbamate functional groups;

$U_4$ is absent or represents an amide or ester linker;

$V_4$ is absent or represents alkyl optionally comprising one or more ether, ester, amine, amide, urea, piperazinyl, sulfonamide or carbamate functional group; and A is —COOH, —PO(OH)$_2$, 26. The copolymeric binder of any one of items 20 to 25, wherein monomer units B are of formula:

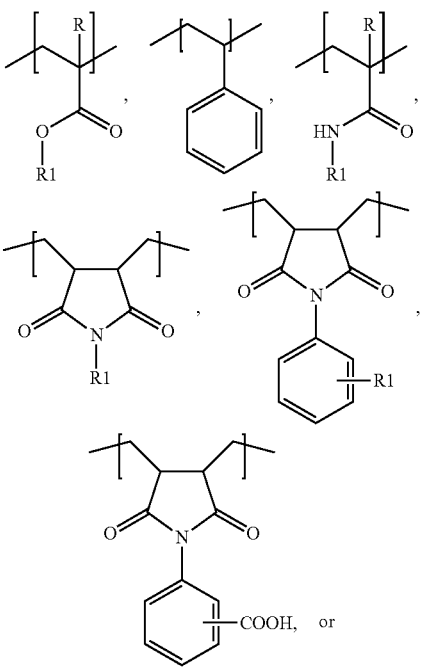

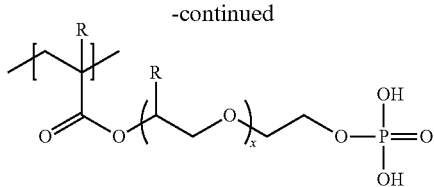

wherein:
R is hydrogen or methyl;
R1 is hydrogen or alkyl; and
x is a number of repeating units between 1 and 10.

27. The copolymeric binder of any one of items 20 to 26, wherein the at least one functional group capable of undergoing a crosslinking reaction via cationic polymerization is N-alkoxymethylamido (such as N-methoxymethylamido), N-hydroxymethylamido, N-alkoxymethylacrylamide (such as N-methoxymethylacrylamide), N-alkoxymethylmethacrylamide (such as N-methoxymethylmethacrylamide), hydroxyl, alkoxy, hydroxyalkyl, epoxy, or oxetane.

28. The copolymeric binder of item 27, wherein monomer units D are of formula:

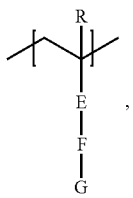

wherein:
R is hydrogen, methyl or ethyl;
E is absent or represents an amide or ester linker;
F is alkyl optionally comprising one or more ether, ester, amine, amide, urea, piperazinyl, or carbamate functional group;
or a poly(ethylene glycol), poly(propylene glycol) and/or poly(ethylene glycol ran propylene glycol) chain, the chain optionally having attached at either or both ends an alkyl optionally comprising one or more ether, ester, amine, amide, urea, piperazinyl, or carbamate functional group; and
G is the functional group capable of undergoing a crosslinking reaction via cationic polymerization.

29. The copolymeric binder of any one of items 20 to 28, wherein monomer units D are of formula:

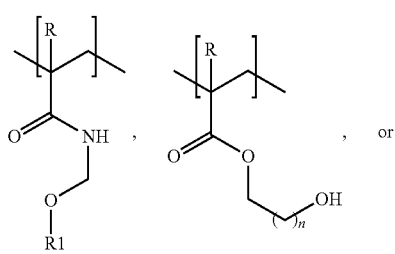

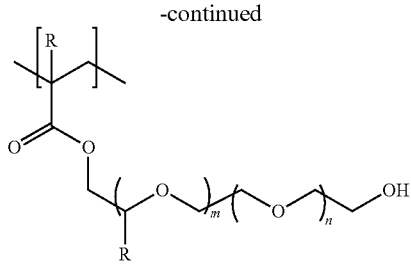

wherein:
R is hydrogen, methyl or ethyl;
R1 is hydrogen or alkyl; and
m and n vary from 1 to 50.

30. The copolymeric binder of any one of item 20 to 29, wherein A5 represents monomer units D.

31. A radiation-sensitive coating composition for a negative-working lithographic printing plate, the composition comprising:
a copolymer as defined in any one of item 1 to 19 and/or a copolymeric binder as defined in any one of items 20 to 30;
a free radical and/or acid generating compound;
a near infrared absorbing compound; and
optional additives.

32. The coating composition of item 31 comprising between about 20 and about 60 w/w % of the copolymer.

33. The coating composition of item 31 or 32 comprising between about 2 and about 30 w/w % of the copolymeric binder.

34. A negative working lithographic offset printing plate comprising a near infrared radiation-sensitive coating, the coating being prepared from a coating composition as defined in any one of item 31 to 33.

35. A negative working lithographic offset printing plate comprising a near infrared radiation-sensitive coating, the coating comprising:
a copolymer as defined in any one of item 1 to 19 and/or a copolymeric binder as defined in any one of items 20 to 30;
a free radical and/or acid generating compound;
a near infrared absorbing dye; and
optional additives.

36. A monomer corresponding to a monomer unit A as defined in any one of items 1, 3-4, 20, and 22-23.

37. A monomer corresponding to a monomer unit B as defined in any one of items 1, 5-7, 20, and 24-26.

38. A monomer corresponding to a monomer unit C as defined in any one of items 1 and 8-12.

39. A monomer corresponding to a monomer unit D as defined in any one of items 1, 13-15, 20, and 27-29.

BRIEF DESCRIPTION OF THE DRAWINGS

In the appended drawings.

DETAILED DESCRIPTION OF THE INVENTION

Copolymers

Figure 1:
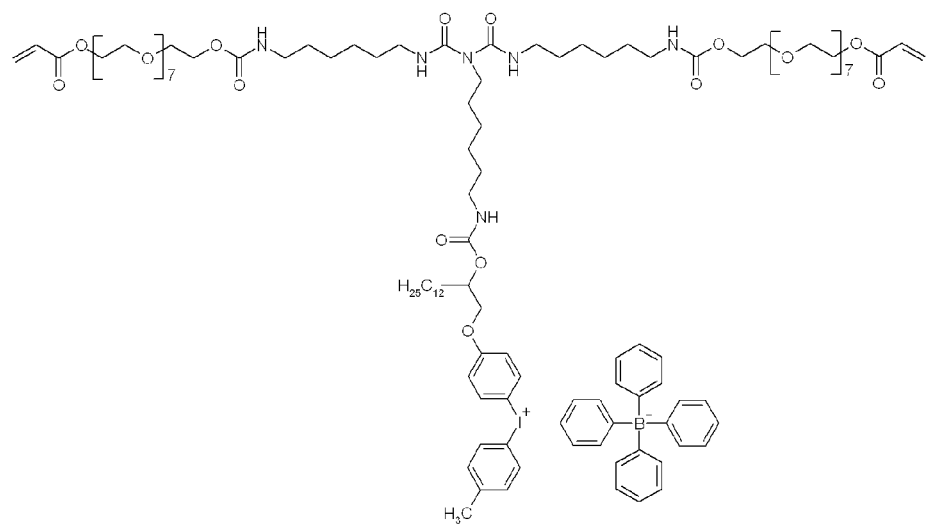
FIGS. 1 to 6 show the reactive iodonium oligomers comprised in Tuxedo® 600 PFB, which is commercially available from American Dye Source, Inc.

Turning now to the present invention in more details, there is provided, in a first aspect, a copolymer comprising monomer units comprising a cyano-containing pendant group in which the cyano is not directly attached to the backbone of the copolymer. In embodiments, the copolymer is for use in near-infrared or UV radiation-sensitive coating compositions for negative-working thermal lithographic printing plates.

As used herein, a copolymer is a polymer made of at least two different types of monomer units. Such monomer units are relatively small molecules that are linked with a relatively large number of other monomer units to form a chain, i.e. a polymer or copolymer. As used herein, the "backbone" of a polymer or copolymer means the series of covalently bonded atoms from the monomer units that together create the continuous chain of the polymer or copolymer. A "pendant group" is a group of atoms attached to, but not part of, the backbone of the copolymer.

As such then, a "cyano-containing pendant group" is a pendant group that comprises a cyano (—C≡N) group. Thus, in the above (as well as in A1 and A2 below), the cyano group, which is comprised in a pendant group, is not directly attached to the backbone of the copolymer; it is rather attached to the pendant group, which is in turns attached to the backbone. More specifically, the monomer unit having a cyano group containing pendant group cannot be

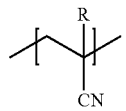

wherein R is any pendant group. Rather, this monomer unit may be of formula:

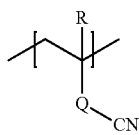

wherein R and Q are any pendant groups.

Herein, a "monomer" is a compound that becomes a monomeric unit upon polymerization. For example,

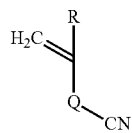

is the monomer producing monomer unit

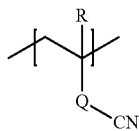

in a polymer or copolymer.

In embodiments, the copolymer comprises:
monomer units A comprising a cyano-containing pendant group in which the cyano is not directly attached to a backbone of the copolymer;

monomer units B comprising a film-forming pendant group, monomer units C comprising a poly(ethylene glycol), poly(propylene glycol) and/or poly(ethylene glycol ran propylene glycol) containing side chain, said side chain being attached to the backbone of the copolymer via an amide, a carbamate, an ester or an urea linker, and optionally, monomer units D comprising at least one functional group capable of undergoing a crosslinking reaction via cationic polymerization.

In embodiments, the copolymer comprises two or more different monomer units of any of the above-listed types of monomer units.

As used herein, a "side chain" is a pendant group that comprise a number of smaller repeating units. More specifically, a "poly(ethylene glycol), poly(propylene glycol) and/or poly(ethylene glycol ran propylene glycol) containing side chain" is a side chain comprising a few poly (ethylene glycol), poly(propylene glycol) and/or poly(ethylene glycol ran propylene glycol) monomer units. Such a side chain can comprise more that one type on monomer units at the same time.

In embodiments, the copolymer has the following general structure:

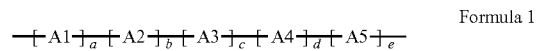

Formula 1 wherein:
a, c, and d are molar ratios varying between about 0.01 and about 0.90;
b and e are molar ratios varying between about 0 and about 0.90;
A1 represents monomer units A;
A2 represents other monomer units A or monomers units B;
A3 represents monomers units C;
A4 represents other monomers units B; and
A5 represents other monomers units B or monomer units D.

The above formula is not meant to specify any type of copolymer (block, alternative, random, etc.). Rather, copolymers of all types are intended to be encompassed by it.

In embodiments, a, b, c, d and/or e are 0.1, 0.2, 0.3, 0.4, 0.5, 0.6, 0.7, or 0.8 or more. In embodiments, a, b, c, d and/or e are 0.8, 0.7, 0.6, 0.5, 0.4, 0.3, 0.2, 0.1 or less.

In the above, b and e can be 0, which means that the A2 and A5 are optional. Thus, in embodiments, A2 and/or A5 are absent from the above chemical structure.

Also, in embodiments, A5 represents only monomers units D.

Monomer Units A

In embodiments, the monomer units A are of formula:

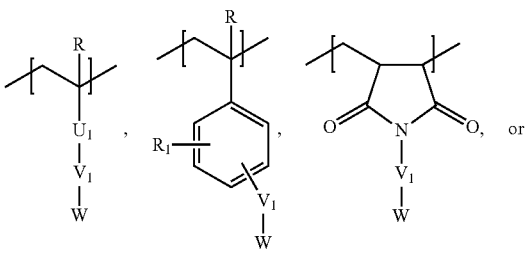

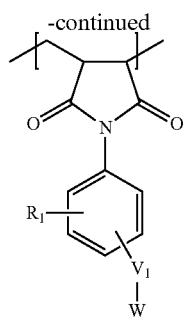

wherein:
R is hydrogen, methyl or ethyl;
$R_1$ is absent or represents one to four alkyl or alkyloxy substituents, the alkyl and alkyloxy substituents optionally comprising one or more ether, ester, amine, amide, urea, piperazinyl, sulfonamide, or carbamate functional groups, the alkyl and alkyloxy substituents optionally being substituted with one or more cyano (in embodiments, the alkyl and alkyloxy substituents have between 1 and 10 carbon atoms);
$U_1$ is an amide or ester linker;
$V_1$ is absent or represents alkyl optionally comprising one or more ether, ester, amine, amide, urea, piperazinyl, or carbamate functional group, the alkyl optionally being substituted with one or more cyano (in embodiments, alkyl has 1 to 15 carbon atoms); and
W is —CN or

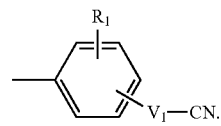

Herein, when it is said that an alkyl comprises (or optionally comprise) a functional group, it means that the functional group may be either at end of the alkyl or in between any two carbon atoms of the alkyl. For more certainty, when more than one functional group is comprised in an alkyl, the functional groups do not need to be separated by carbons atoms of the alkyl; i.e. they may be directly attached to one another. It is understood that when such a functional group (having two available bonds as shown below) is located at an end of the alkyl, one of its two available bonds will be attached to the terminal carbon atom of the alkyl and the other will be attached to a hydrogen atom or to any group to which the alkyl is meant to be attached at that end.

Herein, when it is said that an alkyl is substituted (or optionally substituted) by a group, this expression has its regular meaning in the art, i.e. one of the hydrogen atoms of the alkyl is substituted with the group.

For more certainty, herein an ether functional group is —O—; an ester functional group (or linker) is —(C=O)—O— or —O—(C=O)—; an amine functional group (or linker) is —$NR_3$—, an amide functional group (or linker) is —(C=O)—$NR_3$— or —$NR_3$—(C=O)—; an urea functional group (or linker) is —$NR_3$—(C=O)—$NR_3$—; a piperazinyl functional group (or linker) is

a sulfonamide functional group is —$SO_2$—$NR_3$— or —$NR_3$—$SO_2$—; and a carbamate functional group is —$NR_3$—(C=O)—O— or —O—(C=O)—$NR_3$—. In these functional groups, $R_3$ is hydrogen or alkyl, the alkyl being optionally substituted with one or more hydroxyl, alkyloxy or halide.

In specific embodiments, monomer units A are of formula:

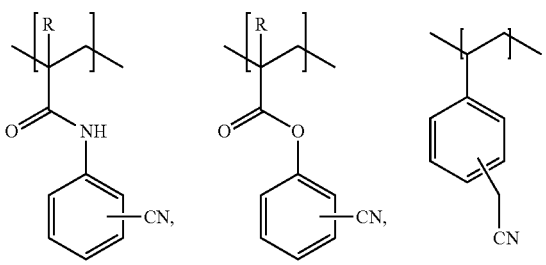

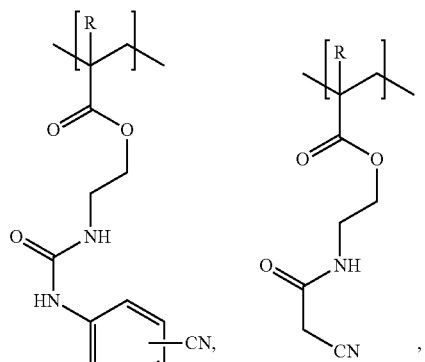

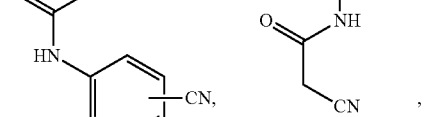

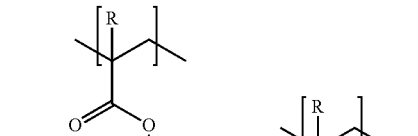

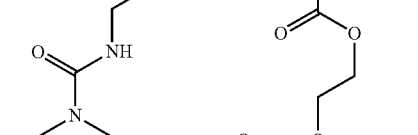

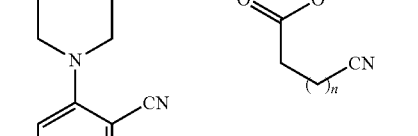

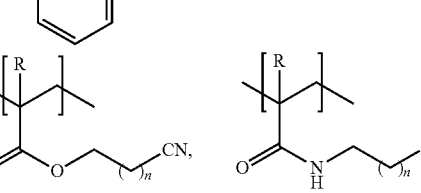

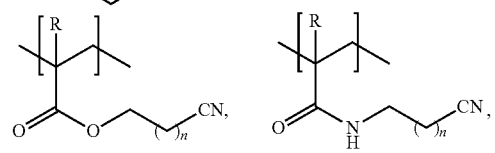

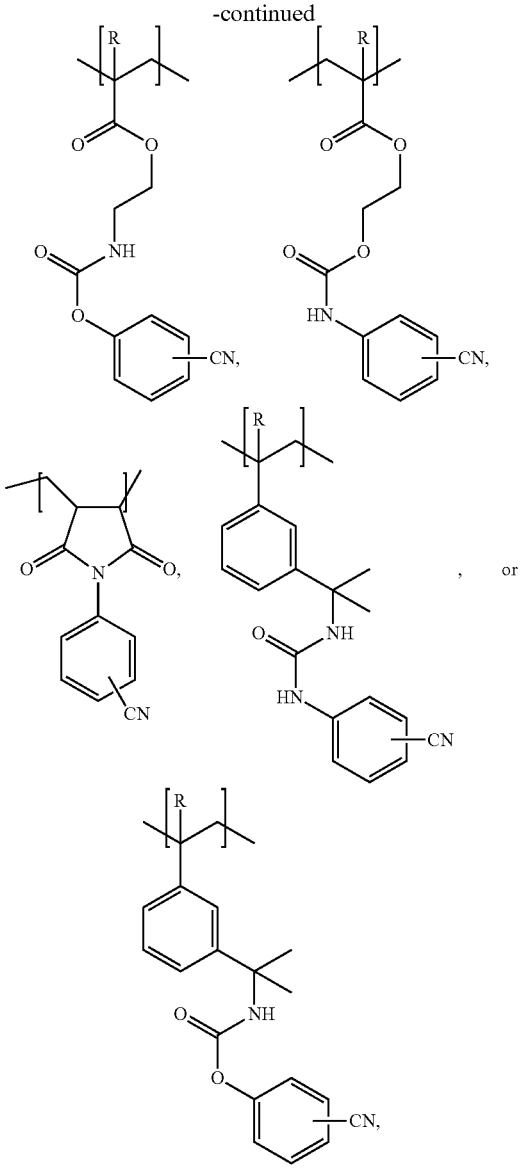

wherein R is hydrogen, methyl or ethyl and n varies between 1 and 10.

In a related aspect, the present invention also relates to monomers. More specifically, the present invention relates to monomers corresponding to any and all of the above-described monomer units A, individually or together as a group, as well as to any and all subsets thereof.

For the sake of concision, the formulas of these monomers are not repeated here. The skilled person will easily infer these formulas from the formulas of the monomer units A given above. Indeed, as used herein, a "monomer" is a compound that becomes a monomeric unit upon polymerization. For example,

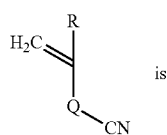

is the monomer producing monomeric unit

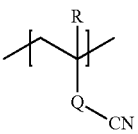

in a polymer or copolymer. The skilled person will easily appreciate that the monomer corresponding to any given monomeric unit will be identical to that monomeric unit except that the two bonds linking the monomeric unit to two other monomer units (to the left and to the right in the above formula) are replaced by a double bond.

Monomer Units B

Monomer units B are monomer units that provide good film forming properties and developability.

In embodiments, monomer units B in A2, A4 and/or A5 are of formula:

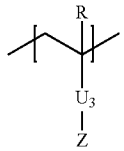

wherein
R is hydrogen, methyl or ethyl;
$U_3$ is absent or represents an amide or ester linker; and
Z is alkyl or aryl,
the alkyl being optionally substituted with one or more hydroxyl, alkyloxy or halide, and
the aryl being optionally substituted with one or more alkyls that are optionally substituted with one or more hydroxyl, alkyloxy or halide.

As can be seen form the above, these monomers units comprise an alkyl or aryl pendant group. The alkyl and aryl groups increase solubility in organic solvents. The solubility of the copolymer in organic solvents can thus be modulated by varying the molar ratio of these monomeric units.

In embodiments, monomer units B in A2, A4 and/or A5 are of formula:

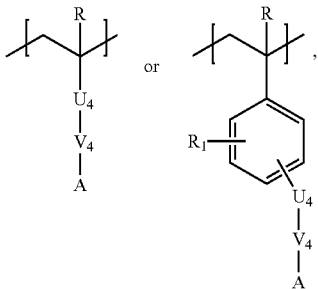

wherein
R is hydrogen, methyl or ethyl;
$R_1$ is absent or represents one to four alkyl substituents;
the alkyl substituents optionally comprising one or more ether, ester, amine, amide, urea, piperazinyl, sulfonamide, or carbamate functional groups;
$U_4$ is absent or represents an amide or ester linker;
$V_4$ is absent or represents alkyl optionally comprising one or more ether, ester, amine, amide, urea, piperazinyl, sulfonamide or carbamate functional group; and A is —COOH, —PO(OH)$_2$,

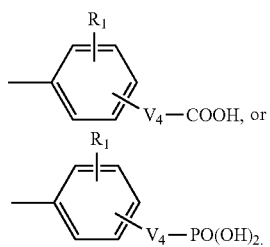

Above, it is meant that V$_4$ include the case where part of the alkyl contain several poly(ethylene glycol), poly(propylene glycol) and/or poly(ethylene glycol ran propylene glycol) repeating units.

Such monomeric units increase solubility in aqueous alkaline solutions as they comprise an acidic functional group, such as a carboxylic acid (—COOH) or a phosphoric acid (—PO(OH)$_2$). The solubility of the copolymer in aqueous alkaline solutions can thus be modulated by varying the molar ratio of these monomeric units.

In embodiments, monomer units B are of formula:

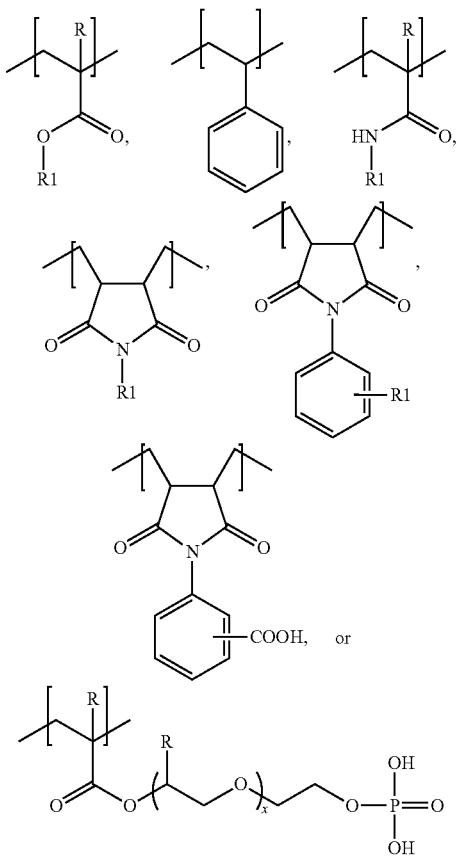

wherein R is hydrogen or methyl, R1 is hydrogen or alkyl (in embodiments, alkyl has 1 to 10 carbon atoms), and x is a number of repeating units between 1 and 10.

In embodiment, monomer units B can be obtained via free radical polymerization of ethylenic monomers including acrylate, methacrylate, alkylacrylate, alkylmethacrylate, acrylamide, methacrylamide, alkylacrylamide, alkylmethacrylamide, styrene and combinations thereof, wherein, in embodiments, alkyl has between 1 and 10 carbon atoms.

In a related aspect, the present invention also relates to monomers. More specifically, the present invention relates to monomers corresponding to any and all of the above-described monomer units B, individually or together as a group, as well as to any and all subsets thereof.

For the sake of concision, the formulas of these monomers are not repeated here. The skilled person will easily infer these formulas from the formulas of the monomer units B given above. Indeed, as used herein, a "monomer" is a compound that becomes a monomeric unit upon polymerization. For example,

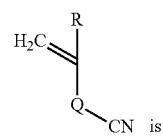

the monomer producing monomeric unit

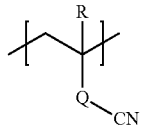

in a polymer or copolymer. The skilled person will easily appreciate that the monomer corresponding to any given monomeric unit will be identical to that monomeric unit except that the two bonds linking the monomeric unit to two other monomer units (to the left and to the right in the above formula) are replaced by a double bond.

Monomer Units C

As stated above, monomer units C comprise a poly(ethylene glycol), poly(propylene glycol) and/or poly(ethylene glycol ran propylene glycol) containing side chain, said side chain being attached to the backbone of the copolymer via an amide, a carbamate, an ester or an urea group.

In embodiments, the side chain of monomer units C is terminated by a hydroxyl group, a methoxy group or a substituent comprising a cyano group. The cyano group promotes adhesion. The hydroxyl and methoxy group can undergo a crosslinking reaction via cationic polymerization. The poly(ethylene glycol), poly(propylene glycol) and/or poly(ethylene glycol ran propylene glycol) containing side chain acts as an internal surfactant. The polymeric particles may be thought of as "hairy balls" in which the side chains are the hairs. These hairs stabilize the polymeric particles in solution.

In embodiments, monomer units C are of formula:

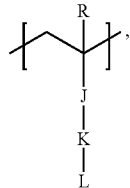

wherein:
R is hydrogen, methyl or ethyl;
J is absent or represents an amide, ester, carbamate or urea linker; and
K and L together form said side chain, K comprising a poly(ethylene glycol), poly(propylene glycol) and/or poly(ethylene glycol ran propylene glycol) chain, and L being a —OH, —OCH₃, —CN or

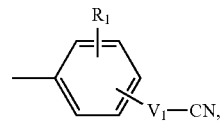

wherein
R₁ is absent or represents one to four alkyl or alkyloxy substituents, the alkyl and alkyloxy substituents optionally comprising one or more ether, ester, amine, amide, urea, piperazinyl, sulfonamide, or carbamate functional groups, the alkyl and alkyloxy substituents optionally being substituted with one or more cyano (in embodiments, the alkyl and alkyloxy substituents have between 1 and 10 carbon atoms); and V₁ is absent or represents alkyl optionally comprising one or more ether, ester, amine, amide, urea, piperazinyl, or carbamate functional group, the alkyl optionally being substituted with one or more cyano (in embodiments, alkyl has 1 to 15 carbon atoms).

In embodiments, one or more ether, ester, amine, amide, urea, piperazinyl, or carbamate linker is attached at either or both ends of the poly(ethylene glycol), poly(propylene glycol) and/or poly(ethylene glycol ran propylene glycol) chain in K. Alternatively or in addition to this linker, in embodiments, an alkyl is attached at either or both ends of the poly(ethylene glycol), poly(propylene glycol) and/or poly (ethylene glycol ran propylene glycol) chain in K, said alkyl optionally comprising one or more ether, ester, amine, amide, urea, piperazinyl, or carbamate functional group. In embodiments, said alkyl has between 1 and 25 carbon atoms.

In more specific embodiments, monomer units C are of formula:

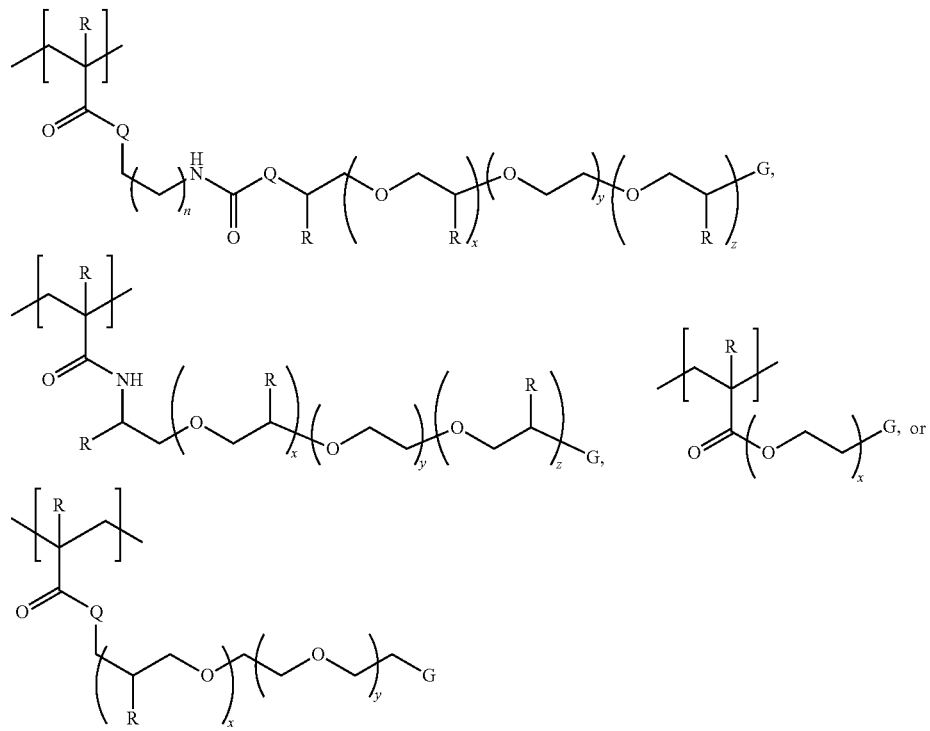

wherein:
R is independently hydrogen, methyl or ethyl;
x, y, and n vary from 1 to 20;
z varies from 0 to 20;
Q is independently

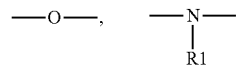

or —O—CH₂CH₂—NH—C(=O)—NH—CH₂—; and
G is hydroxyl, methoxy,

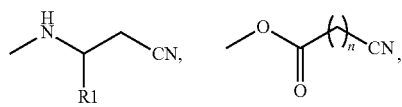

-continued

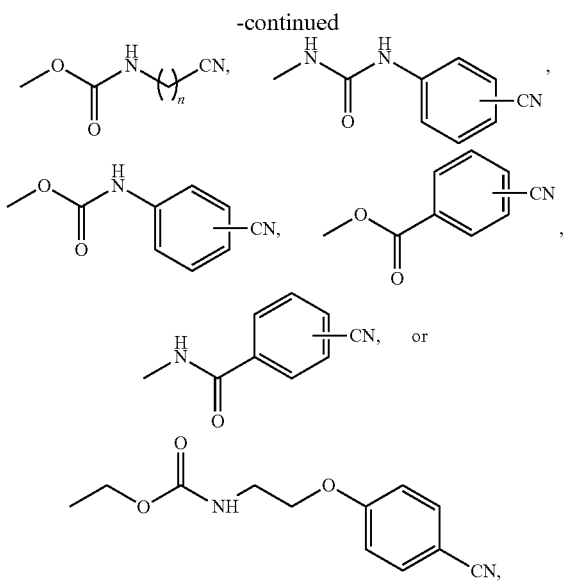

wherein n is as defined above, and
wherein R1 in Q and G is hydrogen or alkyl.

In embodiments, R1 in Q and G is alkyl with 1 to 10 carbon atoms.

In a related aspect, the present invention also relates to monomers. More specifically, the present invention relates to monomers corresponding to any and all of the above-described monomer units C, individually or together as a group, as well as to any and all subsets thereof.

For the sake of concision, the formulas of these monomers are not repeated here. The skilled person will easily infer these formulas from the formulas of the monomer units C given above. Indeed, as used herein, a "monomer" is a compound that becomes a monomeric unit upon polymerization. For example,

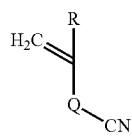

is the monomer producing monomeric unit

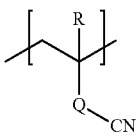

in a polymer or copolymer. The skilled person will easily appreciate that the monomer corresponding to any given monomeric unit will be identical to that monomeric unit except that the two bonds linking the monomeric unit to two other monomer units (to the left and to the right in the above formula) are replaced by a double bond.

Monomeric Units D

As state above, monomer units D comprise at least one functional group capable of undergoing a crosslinking reaction via cationic polymerization.

In embodiments, the at least one functional group capable of undergoing a crosslinking reaction via cationic polymerization in monomer units D is:
N-alkoxymethylamido (such as N-methoxymethylamido),
N-hydroxymethylamido,
N-alkoxymethylacrylamide (such as N-methoxymethylacrylamide),
N-alkoxymethylmethacrylamide (such as N-methoxymethylmethacrylamide),
hydroxyl,
alkoxy,
hydroxyalkyl,
epoxy, or
oxetane,
wherein, in embodiments, alkyl has between 1 and 10 carbon atoms and/or alkoxy has between 1 and 10 carbon atoms.

In embodiments, the monomer units D are of formula:

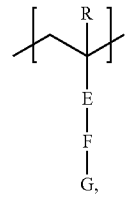

wherein:
R is hydrogen, methyl or ethyl;
E is absent or represents an amide or ester linker;
F is alkyl (comprising in embodiments from 1 to 55 carbon atoms) optionally comprising one or more ether, ester, amine, amide, urea, piperazinyl, or carbamate functional group;
or a poly(ethylene glycol), poly(propylene glycol) and/or poly(ethylene glycol ran propylene glycol) chain, the chain optionally having attached at either or both ends an alkyl (comprising in embodiments from 1 to 10 carbon atoms) optionally comprising one or more ether, ester, amine, amide, urea, piperazinyl, or carbamate functional group; and
G is the functional group capable of undergoing a crosslinking reaction via cationic polymerization.

In more specific embodiments, monomer units D is of formula:

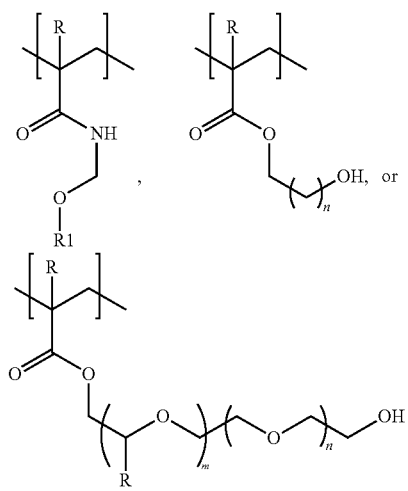

wherein:
R is hydrogen, methyl or ethyl;
R1 is hydrogen or alkyl; and
m and n vary from 1 to 50.

In embodiments, the alkyl in R1 has between about 1 and 10 carbon atoms.

In a related aspect, the present invention also relates to monomers. More specifically, the present invention relates to monomers corresponding to any and all of the above-described monomer units D, individually or together as a group, as well as to any and all subsets thereof.

For the sake of concision, the formulas of these monomers are not repeated here. The skilled person will easily infer these formulas from the formulas of the monomer units D given above. Indeed, as used herein, a "monomer" is a compound that becomes a monomeric unit upon polymerization. For example,

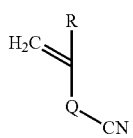

is the monomer producing monomeric unit

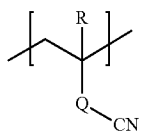

in a polymer or copolymer. The skilled person will easily appreciate that the monomer corresponding to any given monomeric unit will be identical to that monomeric unit except that the two bonds linking the monomeric unit to two other monomer units (to the left and to the right in the above formula) are replaced by a double bond.

Method of Producing the Copolymer

In another aspect, the present invention relates to a method of producing the above-described copolymer. The method comprises the step of copolymerizing copolymerizing monomers corresponding to the constituting monomer units of the desired copolymer in a solvent in which the copolymer is soluble.

The copolymer binder thus can be made by free radical polymerization in organic solvents that can dissolve the formed copolymer to form a homogeneous solution. The organic solvent may be 2-methoxy propanol, ethyl glycol, 1,3-dioxolane, N,N-dimethyl acetamide, 1-methyl-2-pyrrolidinone, and N,N-dimethyl formamide.

Polymeric Particles Comprising the Above Copolymer

In embodiments, the above-described copolymer is in the form of polymeric particles. As used herein, a "polymeric particle" is a small particle made of a polymer or copolymer.

In embodiments, the polymeric particle has a particle size between about 80 and about 1000 nm, and more specifically between about 150 and about 300 nm. In embodiments, the polymeric particle has a particle size of 150, 200, 300, 400, 500, 600, 700, 800 nm or more and/or a particle size of 1000, 900, 800, 700, 600, 400, 300, 200 nm or less.

In embodiments, the polymeric particle is for use in coating compositions and printing plates such as that discussed below.

Method of Producing the Polymeric Particles

In another aspect, the present invention relates to a method of producing the above-described polymeric particles. The method comprises the step of The method comprises the step of copolymerizing monomers corresponding to the monomer units of the copolymer constituting the desired polymeric particles in a solvent in which this copolymer is insoluble.

The polymeric particles thus can be made by free radical polymerization in solvents that cannot dissolve the formed copolymer. In embodiments, the solvent is water and/or an alcohol, such as n-propanol.

Copolymeric Binders

In another aspect, this invention relates to a copolymeric binder comprising:
monomer units A, which are, as described above, monomer units comprising a cyano-containing pendant group in which the cyano is not directly attached to the backbone of the copolymeric binder; and
at least one other type of monomer units.

As used herein, a "copolymeric binder" is a copolymer, which is not in the form of particles and which is used in coating compositions such as that described below to (A) improve the film forming properties of the composition or (B) modify the solubility in aqueous solutions (having pH between 2 and 14) of the coating made from the composition.

As above, the cyano group in the copolymeric binder, which is comprised in a pendant group, is not directly attached to the backbone of the copolymer; it is rather attached to the pendant group, which is attached to the backbone.

In embodiments, the copolymeric binder comprises:
monomer units A;
monomer units B, which are, as described above, monomers units comprising a film-forming pendant group; and
optionally, monomer units D, which are, as described above, monomer units comprising at least one functional group capable of undergoing a crosslinking reaction via cationic polymerization.

In embodiments, the copolymeric binder is of Formula 1 described above in which A3 is omitted. In other words, the copolymeric binder is of Formula 1 wherein c=0, while A1, A2, A4, A5, a, b, d, e, and monomer units A, B, and D are as described above.

Thus the copolymeric binder is of Formula 2:

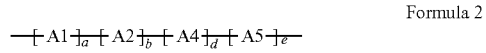

Formula 2 wherein A1, A2, A4, A5, a, b, d, and e are as defined above in regard of Formula 1 and its different embodiments.

In embodiments, the copolymeric binder is for use in coating compositions and printing plates such as that discussed below.

Method of Producing a Copolymeric Binder:

In another aspect, the present invention relates to a method of producing the above-described copolymeric binders. The method comprises the step of copolymerizing monomers corresponding to the constituting monomer units of the desired copolymeric binder in a solvent in which the copolymeric binder is soluble. This copolymerization is carried out in a solvent in which the copolymeric binder is soluble.

The copolymeric binder thus can be made by free radical polymerization in organic solvents that can dissolve the formed copolymeric binder to form a homogeneous solution. The organic solvent may be 2-methoxy propanol, ethyl glycol, 1,3-dioxolane, N,N-dimethyl acetamide, 1-methyl-2-pyrrolidinone, and N,N-dimethyl formamide.

Near Infrared Radiation-Sensitive Coating Composition

In another aspect, the present invention relates to a near infrared radiation-sensitive coating composition for a negative-working lithographic offset printing plate, the composition comprising:
a copolymer as defined above, and/or polymeric particles as defined above and/or a copolymeric binder as defined above;
a free radical and/or acid generating compound;
a near infrared absorbing compound; and
optional additives.

From the above, it should be understood that, in embodiments, the coating composition may comprise a mixture of copolymers, a mixture of polymeric particles, a mixture of copolymeric binders, a mixture of free radical and/or acid generating compound, and/or a mixture of near infrared absorbing compound, as well as optional film-forming additives.

Such coating compositions can be used to prepare a coating for a negative-working lithographic offset printing plate. The coating composition is near infrared radiation-sensitive in that, upon exposure to radiation, there will be a physical or chemical process in the coating (produced using the coating composition) so that 1) the imaged areas will be different from the non-imaged areas after exposure of near infrared radiation and 2) development will produce an image on the printing plate.

In embodiments, the coating composition comprises a total amount of the copolymer and polymeric particles between about 20 and about 60 w/w % and in more specific embodiments a total amount between about 30 and about 50 w/w %.

In embodiments, the coating composition comprises between about 2 and about 30 w/w % of the copolymeric binder and more specifically between about 5 and about 20 w/w % of the binder.

Free Radical and/or Acid Generating Compound

Free radical and/or acid generating compounds are also called free radical and/or cationic initiators in the art. As used herein, a free radical and/or acid generating compound is a compound that generate free radicals, acid, or both acid and free radicals when exposed to near infrared radiation or heat or when receiving an electron. Any such free radical and/or acid generating compound known to the person of skill in the art to be suitable for use in compositions such as the present composition may be used.

Figure 2:
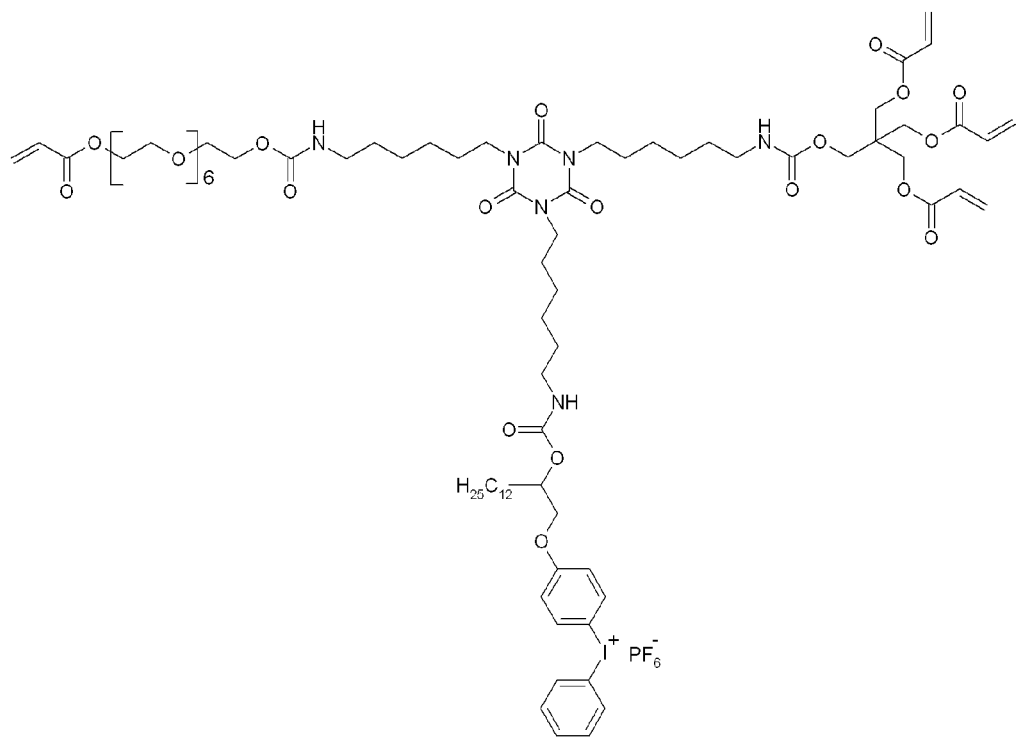
Figure 3:
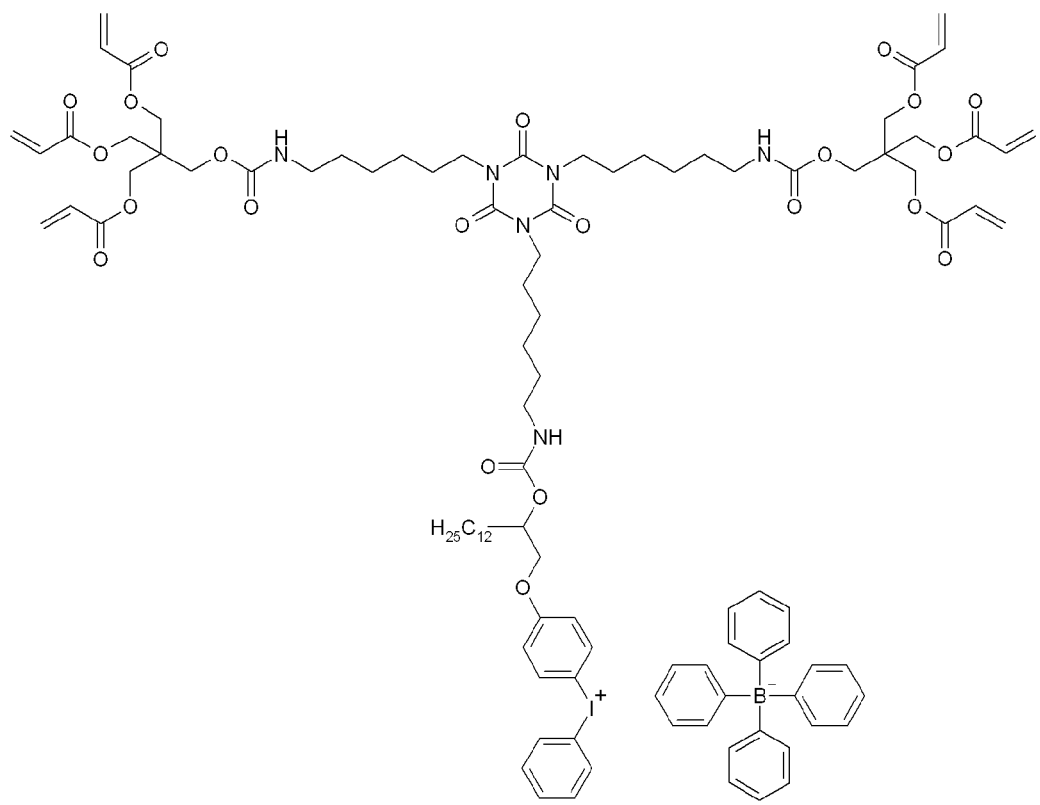
Figure 4:
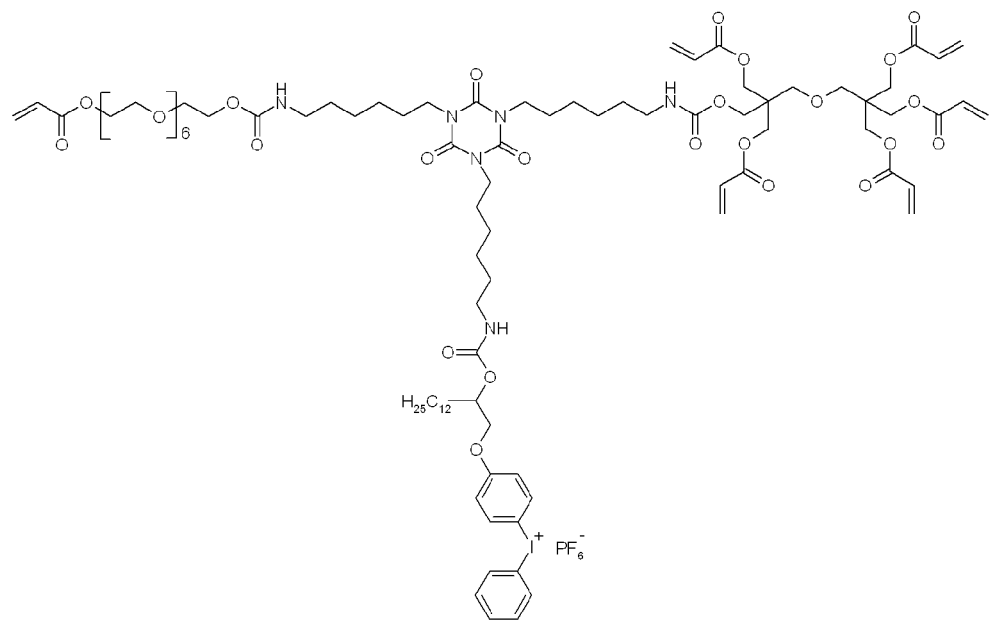
Figure 5:
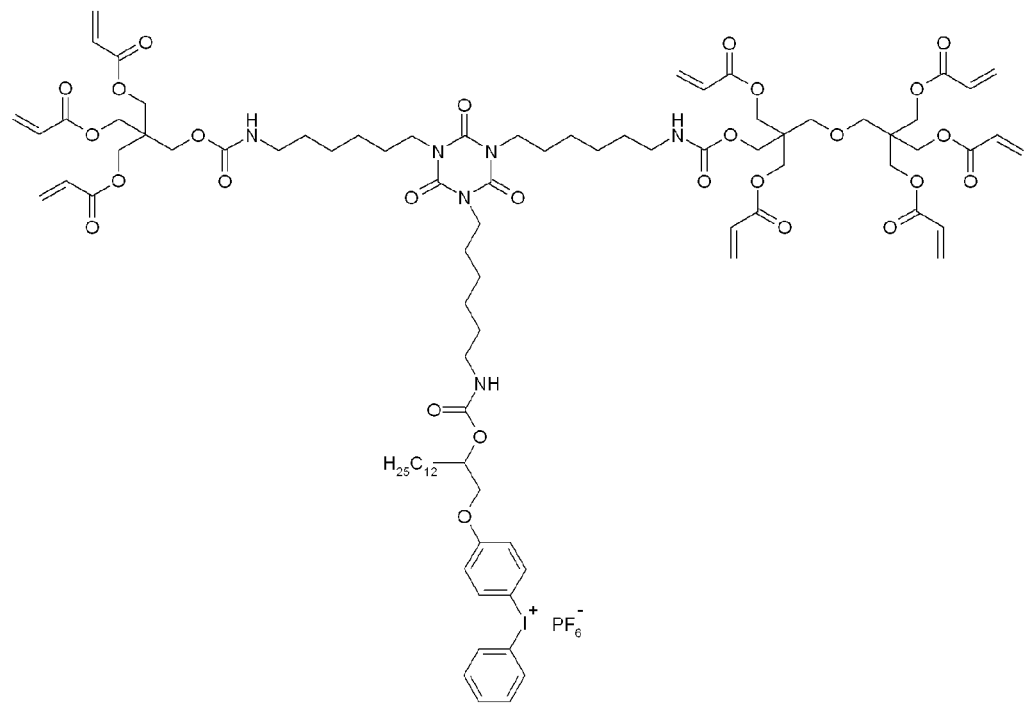
Figure 6:
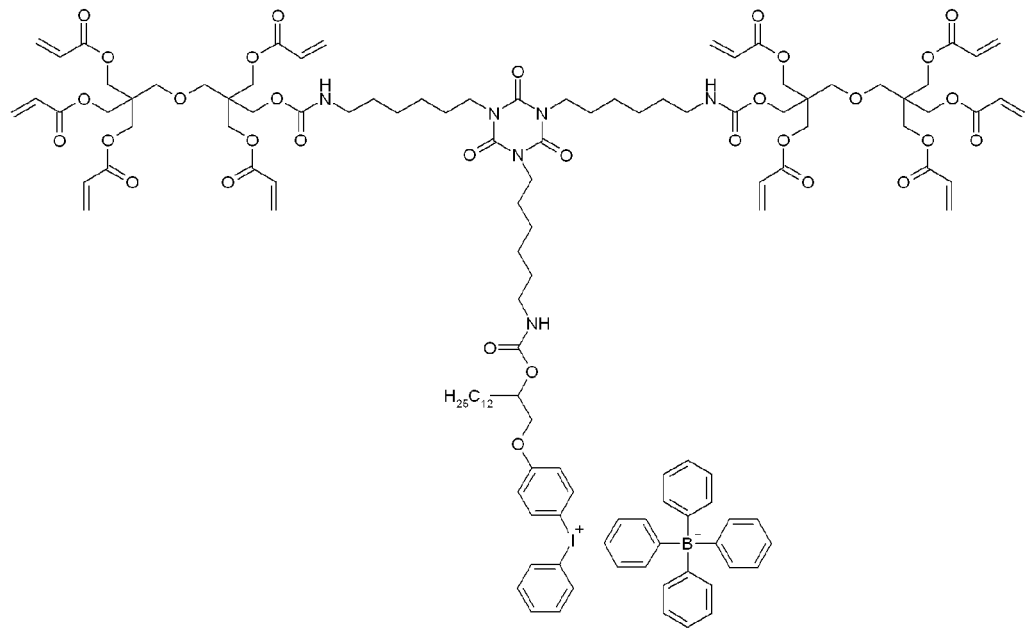

These free radical and/or acid generating compounds may be, for example, the reactive oligomers described in U.S. Patent Applications 2007/0269739, 2008/0171286 and 2009/0035694, which are incorporated herein by reference. For example, the free radical and/or acid generating compounds may be that commercially available from American Dye Source, Inc. (Baie d'Urfe, Quebec, Canada) under trade name Tuxedo® 600 PFB. This product is a mixture of the reactive iodonium oligomers shown in FIGS. 1 to 6. In embodiments, the coating composition comprises between about 20 and about 60 w/w % of such free radical and/or acid generating compound.

These free radical and/or acid generating compounds may also be, for example, acid generating diazo compounds and polymers. These may be the following compound and polymers, some of which are commercially available from PCAS (France):

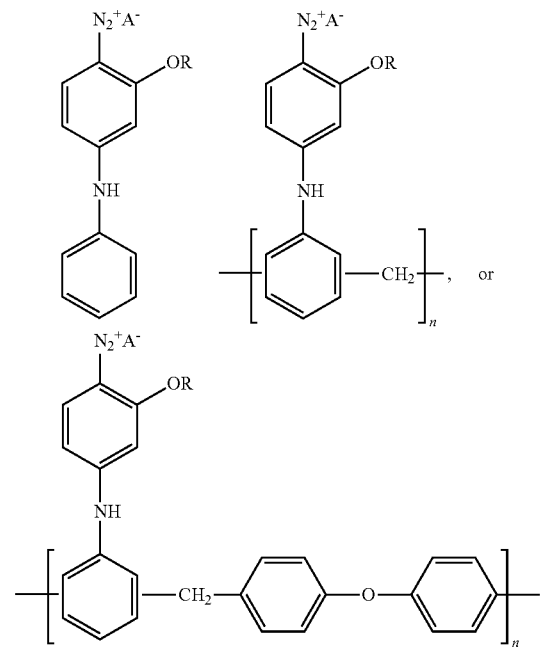

wherein:
A represents $PF_6$, $SbF_6$, aryl sulfonate, alkyl sulfonate and BEI,
R represents linear or branched alkyl or poly(alkylene glycol), and
n represents a number of repeating unit between 1 and 50.
In embodiments, the alkyl has between 1 and 5 carbon atoms and poly(alkylene glycol) has between 1 and 50 repeat units.

In embodiments, these free radical and/or acid generating compounds may also be, for example, free radical generating triazine compounds. These may be the following compounds, some of which are also commercially available from PCAS (France):

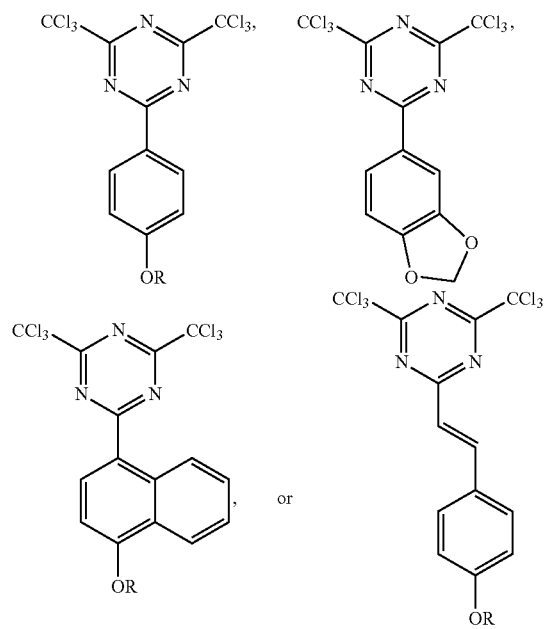

wherein R represents linear or branched alkyl or poly(alkylene glycol). In embodiments, the alkyl and/or alkylene has between 1 and 10 carbon atoms and poly(alkylene glycol) has between 1 and 50 repeat unit.

In embodiments, the coating composition comprises between about 1.0 and about 3.0 w/w % of such diazo and triazine compounds.

Near Infrared Absorbing Compound

The near infrared absorbing compound may be a molecular dye or a polymeric dye. As used herein, a near infrared absorbing compound is a molecular dye or polymeric dye that absorbs near infrared radiation and then produces heat and/or excited electrons that can be donated to free radical and/or acid generating compounds. Any such molecular or polymeric near infrared absorbing dye known to the person of skill in the art to be suitable for use in compositions such as the present composition may be used.

In embodiments, the near infrared absorbing compound may be an azo dye or an aryl amine dye. As used herein, an "azo dye" has its usual meaning in the art. More specifically, the "azo dye" can be understood as being a chromophore comprising an azo functional group, i.e. two double bonded nitrogen atoms: R—N=N—R'. In embodiments, the R and R' groups are aromatic, which helps stabilize the N=N group by making it part of an extended delocalized system.

As used herein, an "aryl amine dye" has its usual meaning in the art. More specifically, the "aryl amine dye" can be understood to be a chromophore comprising an aryl amine group, i.e. an aryl group having attached thereto a nitrogen atom: Aryl-N($R_1$)($R_2$), wherein $R_1$ and $R_2$ independently are hydrogen, alkyl or aryl. In embodiments, alkyl may be linear, branched or cyclic $C_1$-$C_{12}$ and aryl may comprise between 5 and 12 carbon atoms.

In embodiments, the near infrared absorbing compound is one of the following, which are commercially available from American Dye Source, Inc. (Baie d'Urfe, Quebec, Canada):

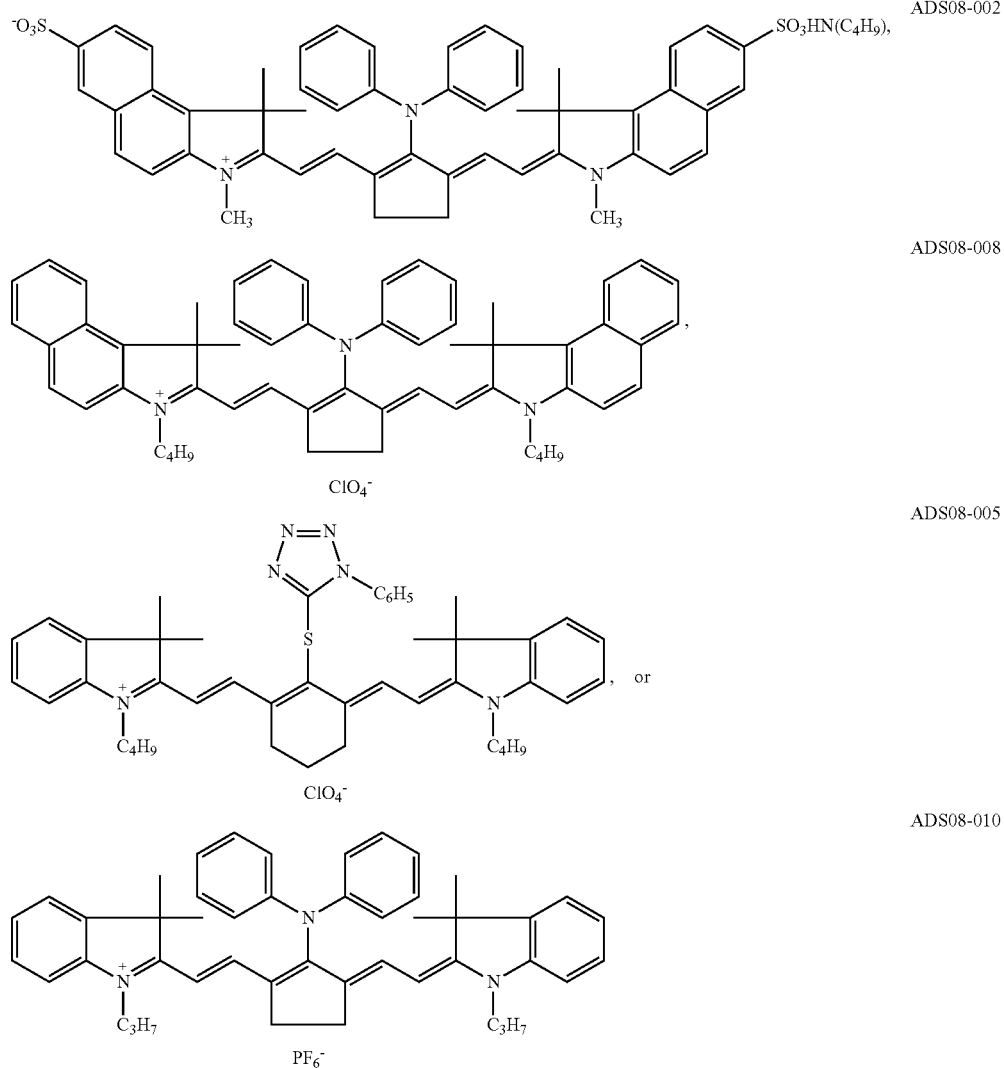

In embodiments, the coating composition comprises between about 1.0 and about 10 w/w % of such infrared absorbing dye, and more specifically between about 2.0 and about 6.0 w/w %.

In embodiments, the near infrared absorbing compound is near infrared absorbing polymeric particles as described in U.S. Patent Application No. 2008/0171286, which is incorporated herein by reference. In embodiments, the coating composition comprises between about 10 and about 50 w/w % of such near infrared absorbing polymeric particles.

Optional Additives

In embodiments, the coating composition further comprises one or more additives. Such additives may be film-forming additives, color formers, stabilizers, pigments, visible dyes and the like. Such additives and their use are well known to the persons of skill in the art.

Thus, the coating composition may comprise, for example, pigments and visible dyes. In embodiments, the pigment is phthalocyanine blue 15:3 dispersed in an acetal copolymer and 2-methoxy propanol solution. This material is commercially available from MyLan Chemicals Inc., Travinh, Vietnam. This pigment dispersion may be used in the coating composition in quantities ranging from 0.5 to 5 w/w %.

The coating composition may also comprise color formers to provide good image printout after laser imaging. Any color former known to the person of skill in the art to be suitable for use in the present composition may be used. The color formers may be the derivatives of triarylpyridine, xanthene and isobenzofuranone. In embodiments, the color formers may be chosen to be colorless and then become colored in the presence of free radical or acid. For example, the color formers may be:

3',6'-bis[N-[2-chlorophenyl]-N-methylamino]spiro[2-butyl-1,1-dioxo[1,2-benzisothiazole-3(3H), 9'-(9H)xanthene]] (prepared by the method of U.S. Pat. No. 4,345,017);

3',6'-bis[N-[2-[methanesulfonyl]phenyl]-N-methylamino] spiro[2-butyl-1,1-dioxo[1,2-benzisothiazole-3(3H),9'-(9H)xanthene]](prepared by the method of U.S. Pat. No. 4,345,017);

9-Diethylamino[spiro[12H-benzo(a)xanthene-12,1'(3'H)-isobenzofuran)-3-one] (available from BF Goodrich, Canada);

2'-di(phenylmethyl)amino-6'-[diethylamino]spiro[isobenzofuran-1(3H), 9'-(9H)-xanthen]-3-one (available from BF Goodrich, Canada);

3-[butyl-2-methylindol-3-yl]-3-[1-octyl-2-methylindol-3-yl]-1-(3H)-isobenzo furanone (available from BF Goodrich, Canada);

6-[dimethylamino]-3,3-bis[4-dimethylamino]-phenyl-(3H)-isobenzofuranone (available from BF Goodrich, Canada);

2-[2-Octyloxyphenyl]-4-[4-dimethylaminophenyl]-6-phenylpyridine (available from BF Goodrich, Canada); or Leuco lactone dyes, such as Blue-63, GN-169 and Red-40, which are available from Yamamoto Chemicals Inc., Japan.

The color formers may be used in the coating compositions in quantities ranging from about 0.5 to about 5 w/w %.

The coating composition may also comprise adhesion promoters to improve the length of run on press. Any adhesion promoter known to the person of skill in the art to be suitable for use in the present composition may be used. The adhesion promoters may be unsaturated oligomers comprising phosphoric acid groups having the following chemical structure:

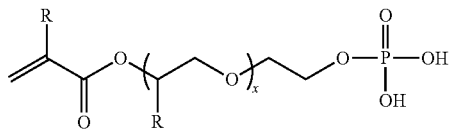

wherein R is hydrogen or methyl and x is a number of repeating units varying from 1 to 10. Such adhesion promoters are commercially available under trade-names: Sipormer® PAM 100 and Sipormer® PAM 200 (available from Rhodia), or Phosmer® A, Phosmer® M, Phosmer® PE, Phosmer® PP, and Phosmer® MH (available from Uni-Chemical Ltd., Japan). The adhesion promoters may be used in the coating compositions in quantities ranging from about 0.5 to about 5 w/w %.

The coating composition may also comprise one or more suitable solvents. This allows forming a coating on a substrate. Any solvent known to the person of skill in the art to be appropriate for this purpose can be used. Non-limiting examples of such solvent include n-propanol, isopropanol, 2-methoxy propanol, ethyl glycol, water or a mixture thereof. The solvent should not dissolve however the polymeric particles.

Negative-Working Lithographic Offset Printing Plate and Method of Producing and Using In another aspect, the present invention relates to a negative-working lithographic offset printing plate comprising a near infrared radiation-sensitive coating, the coating being a coating prepared from the above-described coating composition.

In another related aspect, the present invention relates to a negative-working lithographic offset printing plate comprising a near infrared radiation-sensitive coating, the coating comprising:

1. a copolymer, polymeric particles and/or a copolymeric binder;
2. a free radical and/or acid generating compound as defined above;
3. a near infrared absorbing dye as defined above; and
4. optional additives, all of which being as defined above.

The near infrared radiation-sensitive coating is deposited on a substrate. In embodiments, the substrate is anodized aluminum, plastic films or paper. Aluminum substrates may be brushed-grained or electro-grained, then anodized with acidic solutions. The near infrared radiation-sensitive coating may have a coating weight between about 0.5 and about 2.5 g/m².

In embodiments, there may be one or more layer between the substrate and the near infrared radiation-sensitive coating and/or on top of the near infrared radiation-sensitive coating as known to the person of skill in the art.

For example, a polymeric adhesion-promoting and/or heat-insulating layer may be present between the substrate and the near infrared radiation-sensitive coating. This layer may be obtained from aqueous solutions containing poly (acrylic acid), poly(acrylic acid-co-vinylphosphoric acid) or polyvinyl phosphoric acid, which are then dried using hot air at about 110° C. The coating weight of the adhesion-promoting and/or heat-insulating layer may be between about 0.1 and about 1.0 g/m².

Another example of a layer that can be present on the printing plate in addition to the near infrared radiation-sensitive coating is an overcoat to protect the near infrared radiation-sensitive coating from the environment or provide some other advantage, such as reduced stickiness or improved resistance to scratching.

In another related aspect, the present invention relates to a method of producing a negative-working lithographic offset printing plate, the method comprising the step of: a) providing a substrate, and b) coating a coating composition as defined above on the substrate. In embodiments, the method further comprise the step of coating the substrate with a polymeric adhesion-promoting and/or heat insulating layer before step b).

In another related aspect, the present invention relates to a method of printing, the method comprising the step of: a) providing a negative-working lithographic offset printing plate as defined above, and b) imaging said printing plate with near infrared radiation, c) developing said printing plate and d) using said printing plate on a printing press to print.

The printing plates may be directly imaged with near-infrared laser imaging devices in computer-to-plate and digital offset printing technologies.

In embodiments, the imaged plate is developed off-press with water or a developer. In alternative embodiments, the imaged plate is developed on-press with fountain solutions and inks.

In use, when the near infrared radiation-sensitive coating is imaged with (i.e. exposed to) near infrared radiation, the near infrared absorbing compound will absorb the radiation. The electrons of some of the near infrared absorbing dye molecules will become excited from their ground state to an excited state. The excited electrons of the near infrared absorbing dye molecules can then be donated to the free radical and/or acid generating compound. Some other near infrared dye molecules will decompose and produce heat and some acid. Upon receiving the electrons and/or upon exposure to heat and/or acid, the radical and/or acid generating compound will generate free radicals and/or acid. The polymeric particles, upon exposure to heat, will fuse together, which will make the imaged areas adhere better to the substrate in contrast to the non-imaged areas. In addition, if the copolymer, polymeric particle, the copolymeric binder, the free radical and/or acid generating compound, or any other component in the near infrared radiation-sensitive coating comprises functional groups capable of undergoing crosslinking reactions via cationic polymerization, the generated free radicals and/or acid will cause the polymerization of these compounds. This will result in a 3D crosslinked network in the imaged area. These changes make the image area become less soluble in water or developer (off-press development) or fountain solution and inks (on-press development) in contrast with the non-imaged areas, which will remain soluble. Thus, both these changes in the imaged area will therefore differentiate the imaged areas from the non-imaged areas and allow the development (on- or off-press) of the printing plates.

Some of the compounds described herein may exist as isomers of different types (optical, geometric and/or positional isomers for example). The present invention embraces all such isomers.

Unless otherwise noted, as used herein "alkyl" means a linear or branched alkyl group having 1 to 60 carbon atoms and "aryl" means an aryl group having 1 to 3 cycles and optionally comprising one or two heteroatoms, such as N, O and S. Similarly, "alkyloxy" means a linear or branched alkyloxy (R—O—) group comprising 1 to 60 carbon atoms. In embodiments, the alkyl an alkyloxy have 24, 20, 12, 6 or less carbon atoms. In embodiments, the alkyl and alkyoxy have 6, 12, 20, 24 or more carbon atoms.

Herein, unless otherwise indicated, w/w % values are based on the total dry weight of the coating composition.

As used herein, "near infrared radiation" means electromagnetic radiation, such as that emitted by a laser, with a wavelength between about 700 and about 1100 nm. Non-limiting examples of such near infrared radiation is the light emitted by diode lasers, which are equipped with plate-setters available from Creo-Kodak, Dinippon Screen, Heidelberg and Presstek International.

As used herein, "about" means plus or minus 5% of the numerical value thus qualified.

Other objects, advantages and features of the present invention will become more apparent upon reading of the following non-restrictive description of specific embodiments thereof, given by way of example only with reference to the accompanying drawings.

DESCRIPTION OF ILLUSTRATIVE EMBODIMENTS

The present invention is illustrated in further details by the following non-limiting examples. These examples use the compounds listed in the following glossary.

GLOSSARY

| | |
|---|---|
| ADS08-008 | Near infrared absorbing dye, available from American Dye Source, Inc., Baie d'Urfe, Quebec, Canada having the chemical formula given above. |
| MAM | Methacrylamide, available from Sigma Aldrich, Canada. |
| Blue 63 | Blue Color Former, available from Yamamoto Chemicals Inc., Japan. |
| BMA | n-Butyl methacrylate, available from Sigma Aldrich, Canada. |
| BULT | 4-Butyrolactone, available from Sigma Aldrich. |
| BYK 307 | Solution of a polyether modified polydimethylsiloxane in 2-methoxy propanol, availab.e from BYK Additives & Instruments. |
| CN-BD01 | Copolymeric binder having the structure given below in Example 11, available from American Dye Source, Inc., Baie d'Urfe, Quebec, Canada. |
| CN-M01 | 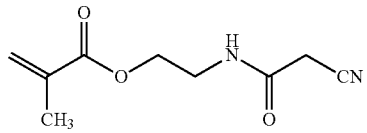<br>Cyanomethylamido-ethyl-methacrylate, available from American Dye Source, Inc., Baie d'Urfe, Quebec, Canada. |
| CN-M02 | 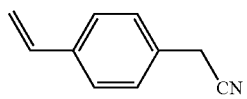<br>4-Vinylbenzyl cyanide, available from American Dye Source, Inc., Baie d'Urfe, Quebec, Canada. |
| CN-M04 | 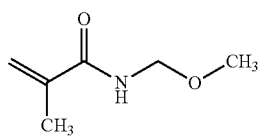<br>N-Methoxy methyl methacrylamide, available from American Dye Source, Inc., Baie d'Urfe, Quebec, Canada. |

| | |
|---|---|
| CN-M05 | Urea linked poly(ethylene glycol-ran-propylene glycol), $M_n$~800, x = 10 and y = 31, available from American Dye Source, Inc., Baie d'Urfe, Quebec, Canada. |
| CN-M07 | Poly(ethylene glycol) 4-cyanophenyl-ethyl-carbamate methacrylate, $M_n$~2100, available from American Dye Source, Inc. Baie d'Urfe, Quebec, Canada |
| CN-M08 | N-(4-cyanophenyl)carbanyl ethyl methacrylate, available from American Dye Source, Inc., Baie d'Urfe, Quebec, Canada |
| Dowanol PM | 2-Methoxy propanol, available from Dow Chemicals, USA. |
| EMA | Ethyl methacrylate, available from Sigma Aldrich, Canada. |
| HEMA | 2-hydroxymethacrylate, available from Sigam Aldrich, Canada. |
| MAA | Methacrylic acid, available from Sigma Aldrich, Canada. |
| MEK | Methyl ethyl ketone, available from Sigma Aldrich, Canada. |
| MMA | Methylmethacrylate, available from Sigma Aldrich, Canada. |
| Styrene | Styrene, available from Sigma Aldrich, Canada. |
| PAM100 | Phosphate esters of polyethylene glycol monomethacrylate, available from Rhodia, USA under trade name Sipomer ® PAM 100. |
| PD08-001 | Phthalocyanine Blue 15:3 dispersed in acetal copolymer (50% pigment and 50% copolymer), available from MyLan Chemicals Inc., Travinh, Vietnam as 20% by solid weight in 2-methoxypropanol solution. |
| Phosmer ® PE | Phosphoric acid containing monomer, wherein x = 4 or 5, available from Uni Chemical Ltd., Japan |
| Tuxedo ® 600PFB | Mixtures of reactive iodonium oligomers, available from American Dye Source, Inc., Baie d'Urfe, Quebec, Canada. See FIGS. 1 to 6. |
| V59 or Vazo 59 | 2,2'-azobis(2-methylbutyronitrile), available from Wako (USA). |

Synthesis of Polymeric Particles and Polymeric Binders

The syntheses of the polymeric particles were performed in a 4 necks glass reactor equipped with a water condenser, a mechanical stirrer, a dropping funnel and a nitrogen or oxygen gas inlet. The molecular structures of the obtained materials were determined by proton NMR and FTIR spectroscopy. The average molecular weight of the copolymers obtained was determined by size exclusion chromatography (SEC), using N,N-dimethylformamide (DMF) solution and calibrated with polystyrene standards. The particle size of polymeric particles was determined by the particle size analyzer (available from Brookhaven Instruments Corporation, Model 90PLUS)

Synthesis of Polymeric Particles

Examples 1 to 6

Polymeric particles having a general structure as shown below:

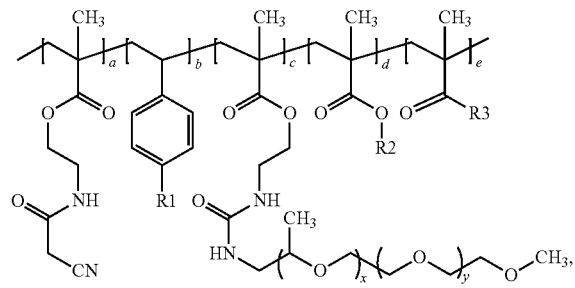

wherein a=0.50 (100 mmoles), b=0.15 (30 mmoles), c=0.02 (4 mmoles), d=0.30 (60 mmoles), e=0.03 (6 mmoles), x=10 and y=31, were synthesized by heating, in a 1 L 4-neck flask at 75° C. under a nitrogen atmosphere with constant high shear stirring, a mixture of 46 grams of n-propanol and 107 grams of de-ionized water in which were dissolved with the corresponding monomers. After heating for 30 minutes, 0.4 g of V59 was added into the reaction mixture. The solution became hazy within 60 minutes of polymerization. After polymerization for 10 hours at 75° C., another 0.5 g of V59 was added into the reaction mixture and the polymerization was continued for another 14 hours. Air was introduced into the reaction mixture and stirring at 75° C. was continued for an additional 2 hours to terminate the polymerization. The molecular weight of the obtained polymeric particles was determined in a tetrahydrofuran solution. The particle size was determined in a isopropanol-water solution (30-70 w/w %).

| Examples | Particles | R1 | R2 | R3 | Particle Size (nm) | Mw (g/mole) |
|---|---|---|---|---|---|---|
| 1 | PP01 | —CH$_2$—CN | —CH$_3$ | —O—C$_2$H$_4$—OH | 300 | 36,000 |
| 2 | PP02 | —CH$_2$—CN | —C$_4$H$_9$ | —O—C$_2$H$_4$—OH | 410 | 39,000 |
| 3 | PP03 | —H | —CH$_3$ | —O—C$_2$H$_4$—OH | 290 | 32,000 |
| 4 | PP04 | —H | —C$_2$H$_5$ | —O—C$_2$H$_4$—OH | 570 | 37,000 |
| 5 | PP05 | —H | —C$_4$H$_9$ | —O—C$_2$H$_4$—OH | 900 | 42,000 |
| 6 | PP06 | —H | —C$_2$H$_5$ | —NH—CH$_2$—OCH$_3$ | 640 | 32,000 |

Examples 7 to 10

Polymeric particles having the general structure below:

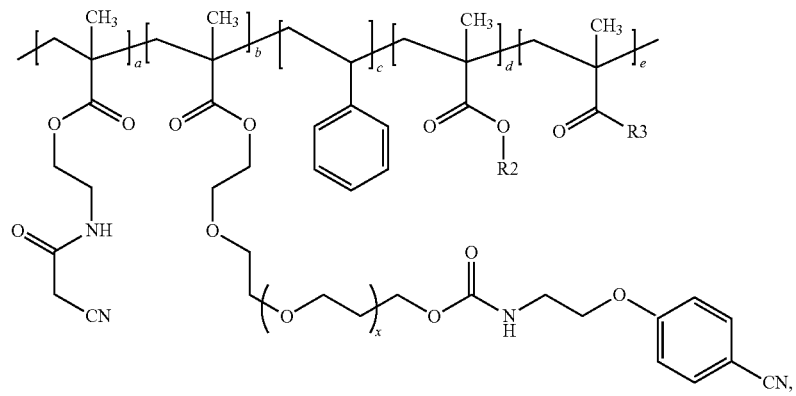

wherein a=0.50 (100 mmoles), b=0.02 (4 mmoles), c=0.20 (40 mmoles), d=0.25 (50 mmoles) and e=0.03 (6 mmoles), were synthesized by heating, in a 1 L 4-neck flask at 75° C. under a nitrogen atmosphere with constant high shear stirring, a mixture of 107 grams of n-propanol and 46 grams of de-ionized water in which were dissolved with the corresponding monomers. After heating for 30 minutes, 0.4 g of V59 was added into the reaction mixture. The solution became hazy within 60 minutes of polymerization. After polymerization for 10 hours at 75° C., another 0.5 g of V59 was added into the reaction mixture and the polymerization was continued for another 14 hours. Air was introduced into the reaction mixture and stirring at 75° C. was continued for an additional 2 hours to terminate the polymerization. The molecular weight of the obtained polymeric particles was determined in a tetrahydrofuran solution. The particle size was determined in a isopropanol-water solution (70-30 w/w %).

| Examples | Particles | R2 | R3 | Particle Size (nm) | Mw (g/mole) |
|---|---|---|---|---|---|
| 7 | PP07 | —CH$_3$ | —O—C$_2$H$_4$—OH | 210 | 32,000 |
| 8 | PP08 | —C$_2$H$_5$ | —O—C$_2$H$_4$—OH | 270 | 34,000 |
| 9 | PP09 | —C$_4$H$_9$ | —O—C$_2$H$_4$—OH | 350 | 40,000 |
| 10 | PP10 | —C$_2$H$_5$ | —NH—CH$_2$—OCH$_3$ | 300 | 35,000 |

Synthesis of Copolymeric Binders

Example 11

A copolymeric binder, CN-BD01, having the following structure:

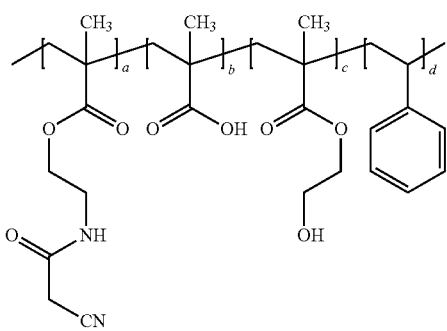

wherein a=0.38, b=0.22, c=0.15, and d=0.25, was prepared by free radical polymerization of 45 grams of cyanomethylacetamido-ethyl-methacrylate, 12.0 grams of methacrylic acid, 12.0 grams of 2-hydroxyethyl methacrylate met and 12.0 grams of styrene in 300 grams of dimethyl acetamide solution at 80° C. under nitrogen atmosphere and constant stirring. Two grams of Vazo 59 were used as free radical initiator. The polymerization was stopped after 24 hours. The average molecular weight of the obtained polymer was 45,000 g/mole as determined by GPC using polystyrene standards. The polymer solution was adjusted with dimethyl acetamide to give 15% solid weight and was then ready for use.

Example 12

The copolymeric binder, CN-BD02, having the chemical structure shown below:

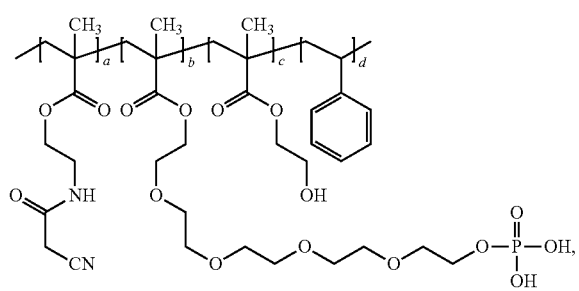

wherein a=0.42, b=0.25, c=0.05, and d=0.27, was prepared by free radical polymerization of 45 grams of cyanomethylacetamido-ethyl-methacrylate, 12.0 grams of Phosmer® PE, 12.0 grams of 2-hydroxyethyl methacrylate and 12.0 grams of styrene in 300 grams of dimethyl acetamide solution at 80° C. under nitrogen atmosphere and constant stirring. Two grams of Vazo 59 were used as free radical initiator. The polymerization was stopped after 24 hours. The average molecular weight of the obtained polymer was 32,000 g/mole as determined by GPC using polystyrene standards. The polymer solution was adjusted with dimethyl acetamide to give 15% solid weight and was then ready for use.

Example 13

A copolymeric binder, CN-BD03, having the structure

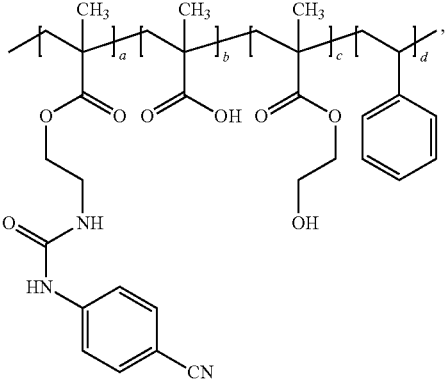

wherein a=0.38, b=0.31, c=0.15, and d=0.16, was prepared by free radical polymerization of 45 grams of N-(4-cyanophenyl)carbonyl ethyl methacrylate, 16.0 grams of methacrylic acid, 12.0 grams of 2-hydroxyethyl methacrylate and 10.0 grams of styrene in 300 grams of dimethyl acetamide solution at 80° C. under nitrogen atmosphere and constant stirring. Two grams of Vazo 59 were used as free radical initiator. The polymerization was stopped after 24 hours. The average molecular weight of the obtained polymer was 47,000 g/mole as determined by GPC using polystyrene standards. The polymer solution was adjusted with dimethyl acetamide to give 15% solid weight and was then ready for use.

Negative-Working Near Infrared Radiation-Sensitive Lithographic Offset Printing Plates Printing plates were produced and tested as follows. The coated plates were imaged using Screen PlateRite 8600S platesetter equipped with 830 nm lasers at 90% laser power and 700 RPM drum speed. The imaged plates were developed off-press by spraying with the gum solution (WG100, available from Agfa, Belgium) or SP200 developer (available from Kodak, USA). The developed plates were mounted on Speed Master 74 press (available from Heidelberg, Germany) using HyPlus 100 black ink (available from Toyo Ink Group, Japan) and fountain solution containing 3.0 parts of MYLAN-FS100 in 97.0 parts of water (available from MyLan Chemicals Inc., Vietnam). The print length of the plates was determined when the 10% dot of the image on the paper was damaged.

Examples 14 to 19

Coating solutions with the compositions shown in Table I were coated on a hydrochloric acid electro-grained, sulfuric acid anodized aluminum substrate, which was treated with NaF/NaH$_2$PO$_4$ solution at 80° C., using wire-wound rod. The coated films were dried at 80° C. with hot air. The obtained coating weight was around 1.0 g/m$^2$.

TABLE I

| | Weight (grams) | | | | | | |
| --- | --- | --- | --- | --- | --- | --- | --- |
| | Ex. 14 | Ex. 15 | Ex. 16 | Ex. 17 | Ex. 18 | Ex. 19 | Ex. 20 |
| Ingredients | | | | | | | |
| PP01 | 2.40 | | | | | | |
| PP02 | | 2.40 | | | | | |
| PP03 | | | 2.40 | | | | |
| PP04 | | | | 2.40 | | 2.40 | 2.40 |
| PP05 | | | | | 2.40 | | |
| PP06 | 2.00 | 2.00 | 2.00 | 2.00 | 2.00 | 2.00 | 2.00 |
| Tuxedo ® 600PFB | 3.50 | 3.50 | 3.50 | 3.50 | 3.50 | 3.50 | 3.50 |
| CN-BD01 | 1.00 | 1.00 | 1.00 | 1.00 | 1.00 | | |
| CN-BD02 | | | | | | 1.10 | |
| CN-BD03 | | | | | | | 1.00 |
| PD08-001 | 0.40 | 0.40 | 0.40 | 0.40 | 0.40 | 0.40 | 0.40 |
| ADS08-008 | 0.40 | 0.40 | 0.40 | 0.40 | 0.40 | 0.40 | 0.40 |
| PAM100 | 0.10 | 0.10 | 0.10 | 0.10 | | | 0.10 |
| Blue 63 | 0.10 | 0.10 | 0.10 | 0.10 | 0.10 | 0.10 | 0.10 |
| Solvents | | | | | | | |
| Dowanol PM | 50.0 | 50.0 | 50.0 | 50.0 | 50.0 | 50.0 | 50.0 |
| MEK | 30.0 | 30.0 | 30.0 | 30.0 | 30.0 | 30.0 | 30.0 |
| BULT | 10.0 | 10.0 | 10.0 | 10.0 | 10.0 | 10.0 | 10.0 |
| Water | 10.0 | 10.0 | 10.0 | 10.0 | 10.0 | 10.0 | 10.0 |
| BYK 307 | 0.10 | 0.10 | 0.10 | 0.10 | 0.10 | 0.10 | 0.10 |
| Printing Test | Print Length on Press | | | | | | |
| Number of copies | <18,000 | <18,000 | ≥25,000 | ≥25,000 | ≥25,000 | ≥25,000 | ≥25,000 |

Examples 21 to 26

Coating solutions with the compositions shown in Table II were coated on a hydrochloric acid electro-grained, sulfuric acid anodized aluminum substrate, which was treated with $NaF/NaH_2PO_4$ solution at 80° C., using wire-wound rod. The coated films were dried at 80° C. with hot air. The obtained coating weight was around 1.0 g/m$^2$.

The plates from Examples 14 to 26 were also mounted on press right after laser imaging. The plates provided clean and high-resolution images on paper after about 50 revolutions. The number of copies obtained in this case was similar to that when the plates when developed off-press.

Although the present invention has been described hereinabove by way of specific embodiments thereof, it can be modified, without departing from the spirit and nature of the subject invention as defined in the appended claims.

TABLE II

| | Weight (grams) | | | | | |
| --- | --- | --- | --- | --- | --- | --- |
| | Ex. 21 | Ex. 22 | Ex. 23 | Ex. 24 | Ex. 25 | Ex. 26 |
| Ingredients | | | | | | |
| PP07 | 2.40 | | | | | |
| PP08 | | 2.40 | | | 2.40 | 2.40 |
| PP09 | | | 2.40 | | | |
| PP10 | | | | 2.40 | | |
| PP06 | 2.00 | 2.00 | 2.00 | 2.00 | 2.00 | 2.00 |
| Tuxedo ® 600PFB | 3.50 | 3.50 | 3.50 | 3.50 | 3.50 | 3.50 |
| CN-BD01 | 1.00 | 1.00 | 1.00 | 1.00 | | |
| CN-BD03 | | | | | 1.00 | 1.00 |
| PD08-001 | 0.40 | 0.40 | 0.40 | 0.40 | 0.40 | 0.40 |
| ADS08-008 | 0.40 | 0.40 | 0.40 | 0.40 | 0.40 | 0.40 |
| PAM100 | 0.10 | 0.10 | 0.10 | 0.10 | | |
| Blue 63 | 0.10 | 0.10 | 0.10 | 0.10 | 0.10 | 0.10 |
| Solvents | | | | | | |
| Dowanol PM | 50.0 | 50.0 | 50.0 | 50.0 | 50.0 | 50.0 |
| MEK | 30.0 | 30.0 | 30.0 | 30.0 | 30.0 | 30.0 |
| BULT | 10.0 | 10.0 | 10.0 | 10.0 | 10.0 | 10.0 |
| Water | 10.0 | 10.0 | 10.0 | 10.0 | 10.0 | 10.0 |
| BYK 307 | 0.10 | 0.10 | 0.10 | 0.10 | 0.10 | 0.10 |
| Printing Test | Print Length on Press | | | | | |
| Number of copies | ≥25,000 | ≥25,000 | ≥25,000 | ≥25,000 | ≥25,000 | ≥25,000 |

REFERENCES

The present description refers to a number of documents, the content of which is herein incorporated by reference in their entirety.

| European Patents No. | US Patents No. | U.S. Patent Application Publications No. |
|---|---|---|
| 0 770 495 | 5,569,573 | 2005/0123853 |
| | 6,124,425 | 2007/0269739 |
| | 6,177,182 | 2008/0171286 |
| | 6,261,740 | 2009/0035694 |
| | 6,582,882 | 2009/0111051 |
| | 6,805,052 | 2009/0186299 |
| | 6,846,614 | |
| | 6,899,994 | |
| | 6,960,422 | |
| | 6,969,575 | |
| | 6,983,694 | |
| | 7,001,704 | |
| | 7,261,998 | |

The invention claimed is:

1. A copolymer of Formula 1:

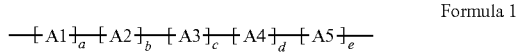

Formula 1 wherein:
a, c, d, and e are molar ratios varying between about 0.01 and about 0.90;
b is a molar ratio varying between about 0 and about 0.90;
A1 represents monomer units A, wherein monomer units A comprise a cyano-containing pendant group in which the cyano is not directly attached to the backbone of the copolymer;
A2 represents monomer units A or monomer units B, wherein monomer units B comprise a film-forming pendant group;
A3 represents monomer units C, wherein monomer units C comprise a poly(ethylene glycol), poly(propylene glycol) and/or poly(ethylene glycol ran propylene glycol) containing side chain terminated by a substituent comprising a cyano group, said side chain being attached to the backbone of the copolymer via an amide, a carbamate, an ester or a urea linker;
A4 represents monomer units B; and
A5 represents monomer units D, wherein monomer units D comprise at least one functional group capable of undergoing a crosslinking reaction via cationic polymerization,
wherein monomer units A in A1 and A2 are different from each other and wherein monomer units B in A2 and A4 are different from each other;
wherein each of the structural groups A1 through A5 are different from one another;
wherein monomer units A are of formula:

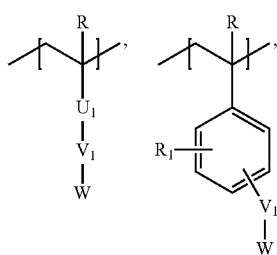

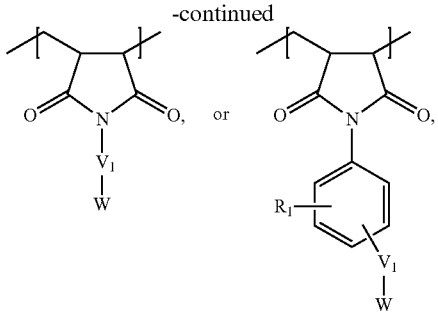

-continued wherein:
R is hydrogen, methyl or ethyl;
$R_1$ is absent or represents one to four substituents, the substituents each independently being alkyl or alkyloxy, the alkyl and alkyloxy substituents optionally comprising one or more ether, ester, amine, amide, urea, piperazinyl, sulfonamide, or carbamate functional groups, the alkyl and alkyloxy substituents optionally being substituted with one or more cyano;
$U_1$ is an amide or ester linker;
$V_1$ is absent or represents alkyl optionally comprising one or more ether, ester, amine, amide, urea, piperazinyl, or carbamate functional group, the alkyl optionally being substituted with one or more cyano; and
W is —CN or

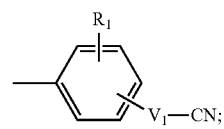

wherein monomer units B are of formula:

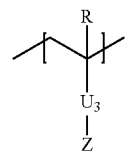

wherein
R is hydrogen, methyl or ethyl;
$U_3$ is absent or represents an amide or ester linker; and
Z is alkyl or aryl,
the alkyl being optionally substituted with one or more hydroxyl, alkyloxy or halide, and
the aryl being optionally substituted with one or more alkyls that are optionally substituted with one or more hydroxyl, alkyloxy or halide;
or
wherein monomer units B are of formula:

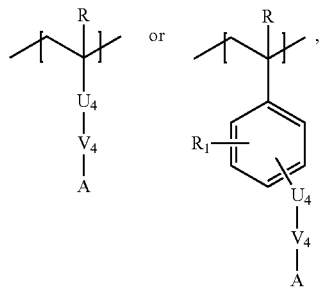

wherein
R is hydrogen, methyl or ethyl;
$R_1$ is absent or represents one to four substituents; the substituents each independently being alkyl optionally comprising one or more ether, ester, amine, amide, urea, piperazinyl, sulfonamide, or carbamate functional groups;
$U_4$ is absent or represents an amide or ester linker;
$V_4$ is absent or represents alkyl optionally comprising one or more ether, ester, amine, amide, urea, piperazinyl, sulfonamide or carbamate functional group; and
A is —COOH, —PO(OH)$_2$,

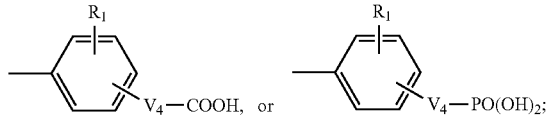

wherein monomer units C are of formula:

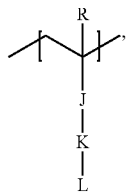

wherein:
R is hydrogen, methyl or ethyl;
J represents an amide, ester, carbamate or urea linker; and
K and L together form said side chain, K comprising a poly(ethylene glycol), poly(propylene glycol) and/or poly(ethylene glycol ran propylene glycol) chain; and
L being
—CN or

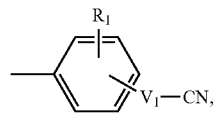

wherein $R_1$ is absent or represents one to four substituents, the substituents each independently being alkyl or alkyloxy, the alkyl and alkyloxy substituents optionally comprising one or more ether, ester, amine, amide, urea, piperazinyl, sulfonamide, or carbamate functional groups, the alkyl and alkyloxy substituents optionally being substituted with one or more cyano; and
$V_1$ is absent or represents alkyl optionally comprising one or more ether, ester, amine, amide, urea, piperazinyl, or carbamate functional group, the alkyl optionally being substituted with one or more cyano; and
wherein monomer units D are of formula:

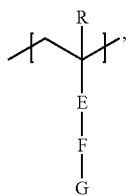

wherein:
R is hydrogen, methyl or ethyl;
E is absent or represents an amide or ester linker;
F is alkyl optionally comprising one or more ether, ester, amine, amide, urea, piperazinyl, or carbamate functional group;
or a poly(ethylene glycol), poly(propylene glycol) and/or poly(ethylene glycol ran propylene glycol) chain, the chain optionally having attached at either or both ends an alkyl optionally comprising one or more ether, ester, amine, amide, urea, piperazinyl, or carbamate functional group; and
G is the functional group capable of undergoing a cross-linking reaction via cationic polymerization.

2. The copolymer of claim 1, wherein, in monomer units C, one or more ether, ester, amine, amide, urea, piperazinyl, or carbamate linker is attached at either or both ends of the poly(ethylene glycol), poly(propylene glycol) and/or poly(ethylene glycol ran propylene glycol) chain.

3. The copolymer of claim 1, wherein, in monomer units C, an alkyl is attached at either or both ends of the poly(ethylene glycol), poly(propylene glycol) and/or poly(ethylene glycol ran propylene glycol) chain, said alkyl optionally comprising one or more ether, ester, amine, amide, urea, piperazinyl, or carbamate functional group.

4. The copolymer of claim 1, wherein the copolymer is in the form of polymeric particles.

5. The copolymer of claim 1, wherein monomer units D are of formula:

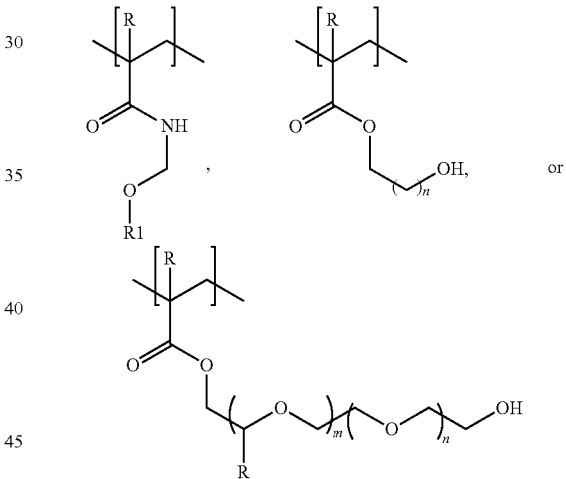

wherein:
R is hydrogen, methyl or ethyl;
R1 is hydrogen or alkyl; and
m and n vary from 1 to 50.

6. The copolymer of claim 1, wherein monomer units A are of formula:

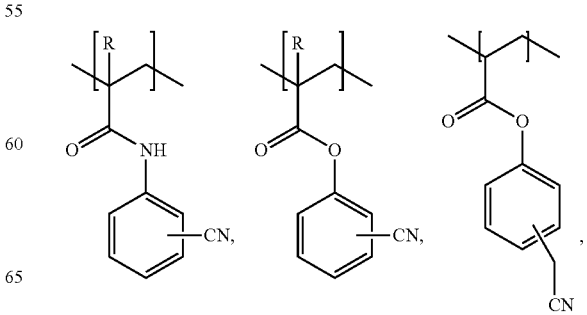

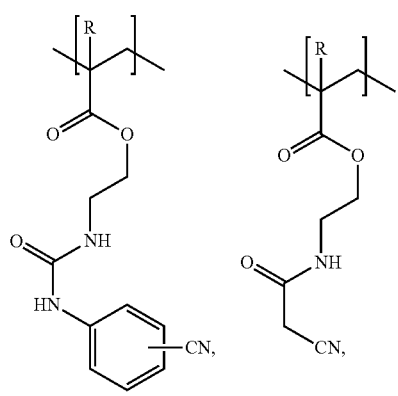
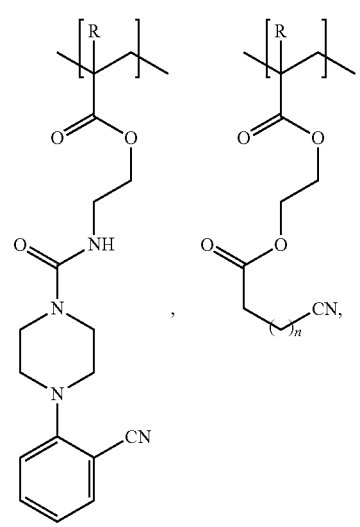
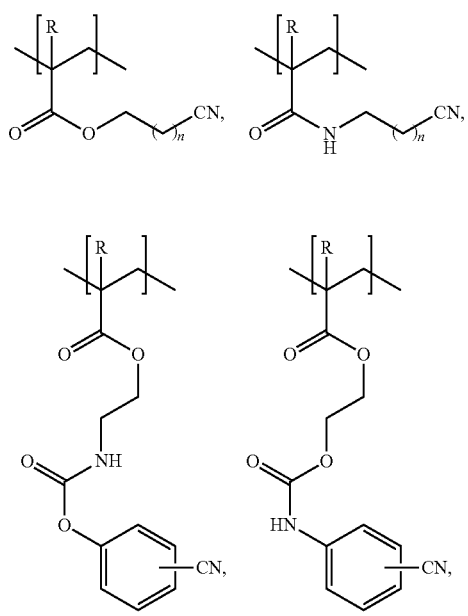
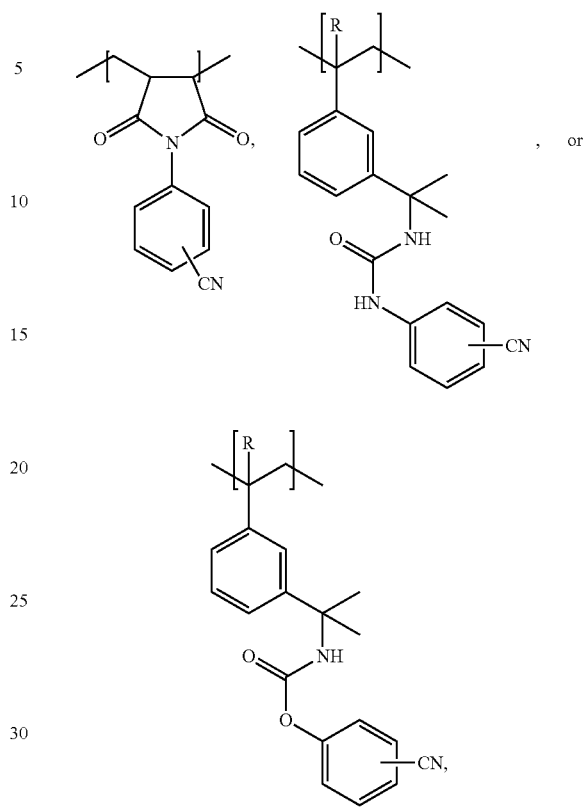
wherein R is hydrogen, methyl or ethyl and n varies between 1 and 10.
7. The copolymer of claim 1, wherein monomer units B are of formula:
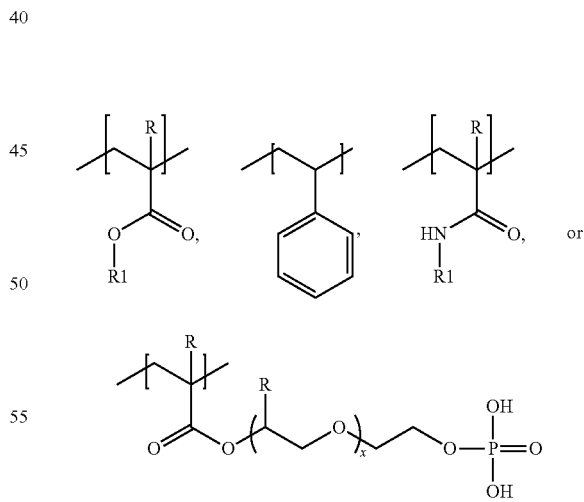
wherein
R is hydrogen or methyl;
R1 is hydrogen or alkyl; and
x is a number of repeating units between 1 and 10.
8. The copolymer of claim 1, wherein monomer units C are of formula:

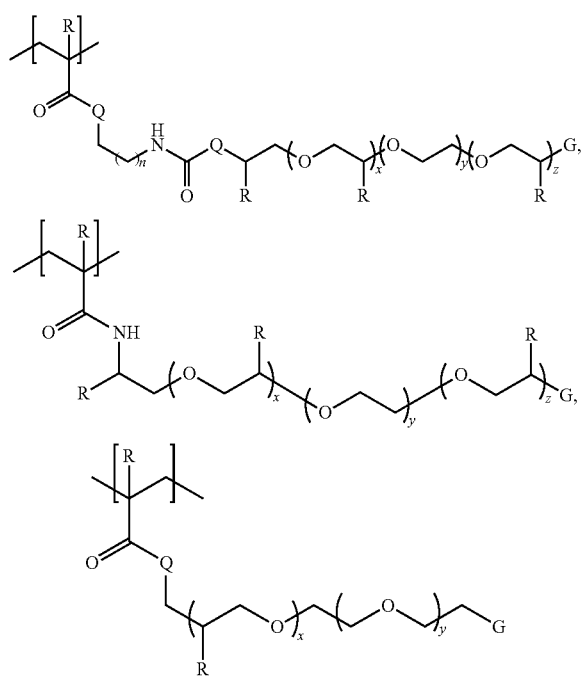

wherein:

R is independently hydrogen, methyl or ethyl;

x, y, and n vary from 1 to 20;

z varies from 0 to 20;

Q is independently or

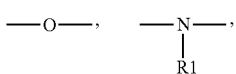

or —O—CH$_2$CH$_2$—NH—C(=O)—NH—CH$_2$—; and

G is:

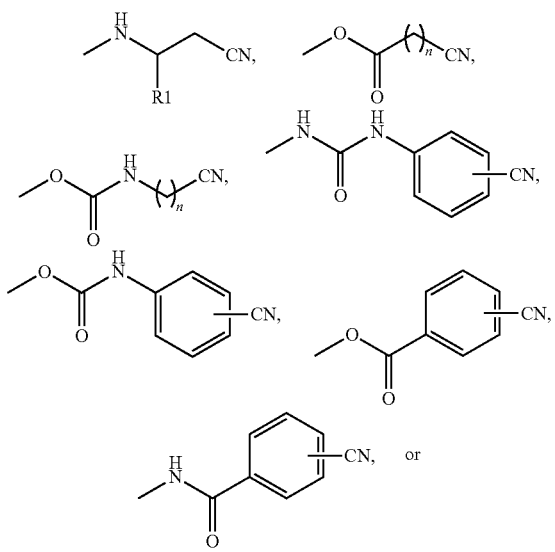

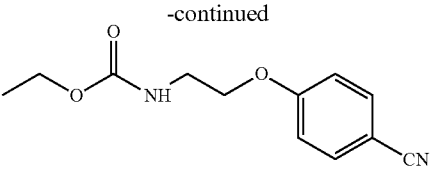

wherein n is as defined above, and wherein R1 in Q and G is hydrogen or alkyl.

9. The copolymer of claim 1, wherein the at least one functional group capable of undergoing a crosslinking reaction via cationic polymerization is N-alkoxymethylamido, N-hydroxymethylamido, N-alkoxymethylacrylamide, N-alkoxymethylmethacrylamide, hydroxyl, alkoxy, hydroxyalkyl, epoxy, or oxetane.

10. The copolymer of claim 4, wherein the polymeric particles have a particle size between about 80 and about 1000 nm.

11. The copolymer of claim 10, wherein the polymeric particles have a particle size between about 150 and about 300 nm.

12. The copolymer of claim 1, wherein monomer units C are of formula:

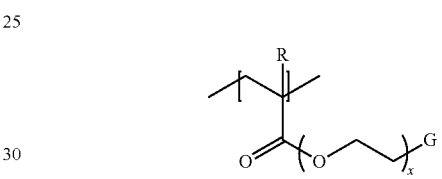

wherein:

G is:

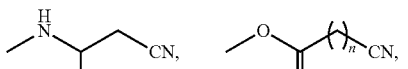

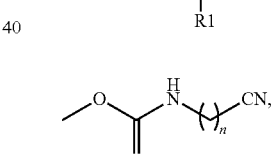

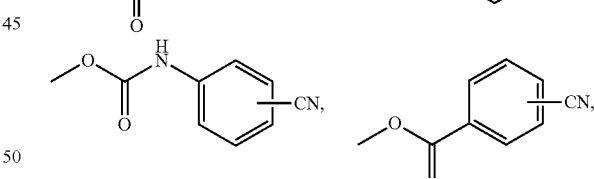

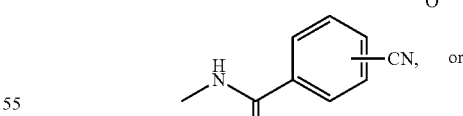

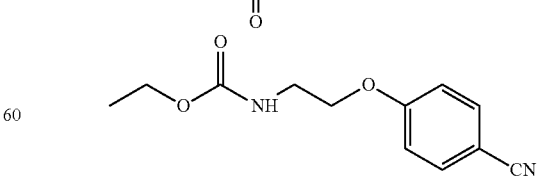

wherein n varies from 1 to 20, and wherein R1 in G is hydrogen or alkyl.

\* \* \* \* \*